(12) United States Patent
El Saharty et al.

(10) Patent No.: US 6,569,469 B1
(45) Date of Patent: May 27, 2003

(54) AGENT FOR STABILIZING FOODSTUFFS AND COSMETIC AGENTS, AND A METHOD FOR THE PRODUCTION THEREOF

(75) Inventors: Yasser El Saharty, Cairo (EG); Ulrich Krings, Brokeloh (DE); Ralf Günther Berger, Hannover (DE)

(73) Assignee: Universität Hannover (DE)

( * ) Notice: Subject to any disclaimer, the term of this patent is extended or adjusted under 35 U.S.C. 154(b) by 0 days.

(21) Appl. No.: 09/762,139

(22) PCT Filed: Jul. 26, 1999

(86) PCT No.: PCT/DE99/02258
§ 371 (c)(1),
(2), (4) Date: Mar. 14, 2001

(87) PCT Pub. No.: WO00/07464
PCT Pub. Date: Feb. 17, 2000

(30) Foreign Application Priority Data

Aug. 1, 1998 (DE) .......................................... 198 34 764

(51) Int. Cl.⁷ .......................... A61K 35/78; A61K 47/00
(52) U.S. Cl. ....................... 424/750; 424/776; 424/725; 514/783
(58) Field of Search ............................... 424/725, 750, 424/776; 514/783

(56) References Cited

U.S. PATENT DOCUMENTS 1,836,858 A * 12/1931 Massatsch et al.
1,873,709 A * 8/1932 Hoffman
5,919,511 A * 7/1999 Hagiwara .................... 426/590

FOREIGN PATENT DOCUMENTS

JP 02003495 A * 1/1990

OTHER PUBLICATIONS

Kajimoto, G. et al. "Antioxidant effects of barley aqeous extract on the oxidative deterioration of oil." Nippon EIYO Shokuryo Gakkaishi—Journal of Japanese Society of Nutrition and Food Science, vol. 44, No. 11, 1997, pp. 788–794.*

* cited by examiner

Primary Examiner—Jean C. Witz
Assistant Examiner—Patricia Patten
(74) Attorney, Agent, or Firm—Pendorf & Cutliff

(57) ABSTRACT

The invention relates to a method for producing an antioxidatively active extract which can be used in particular for stabilizing foodstuffs and cosmetic agents. According to the method, non-enzymatically browned grain germs, or a mixture containing non-enzymatically browned grain germs, is/are extracted using a solvent or solvent mixture (e.g. ethanol or an ethanolic mixture) having an $E_T^N$ value ranging from 0.6 to 0.8, and the extracting agent is then optionally separated off. The invention also relates to a method for stabilizing unbrowned grain germs in which these unbrowned grain germs are mixed with non-enzymatically browned grain germs.

11 Claims, 17 Drawing Sheets

AGENT FOR STABILIZING FOODSTUFFS AND COSMETIC AGENTS, AND A METHOD FOR THE PRODUCTION THEREOF

BACKGROUND OF THE INVENTION

1. Field of the Invention

The invention concerns an agent for stabilizing foodstuffs and cosmetic agents as well as a process for production thereof.

Lipid-rich foodstuffs and cosmetic agents can become rancid in particular as a result of a lipid-peroxidation processes (autooxidation). The rancidification of foodstuffs (frequently recognized by their prickly, unpleasant taste) and cosmetic agents results in their becoming unusable.

2. Description of the Related Art

It is already known to add natural or synthetic antioxidants to foodstuffs and cosmetic agents in order to inhibit their autooxidation. Typical anitoxidants are, for example, tert-butylmethoxyphenol (tert-butylhydroxyanisol, BHA) and di-tert-butylmethylphenol (Butylhydroxy-toluol, BHT), ester of gallic acid, tocopherol (vitamin E) as well as ascorbic acid and their fat soluble esters. There is however a great demand for further antioxidants, and in particular for those which can be added to foodstuffs, without having the legal character of a listed food additive which requires regulatory approval.

SUMMARY OF THE INVENTION

It was the task of the present invention to provide an antioxidant which is in particularly suitable for stabilizing lipid-rich foodstuffs.

This task is inventively solved by the provision of an antioxidation effective extract, wherein the extract can be produced by extracting non-enzymatically browned grain germs, or a mixture containing non-enzymatically browned grain germs, using a solvent or solvent mixture having an $E_T^N$-value ranging from 0.6 to 0.8 and optionally separating off the extraction agent.

For $E_T^N$-value and its determination, see Christian Riechhardt, Chem. Rev. 1994, 2319–2358.

The grain germs are preferably separated from the chaff of the grains in conventional manner prior to roasting, in particular separated from the cortex, the epidermis (seed cover, bran), the endosperm (starch and gluten) and the aleurone layer, since these residual components take up a large volume in comparison to the germ and thereby raise the cost of the roasting process.

In accordance with a suitable process according to the invention for production of an antioxidative effective extract, non-enzymatic browned grain germs or a mixture, which includes non-enzymatic browned grain germs, are extracted with a solvent or solvent mixture having a $E_T^N$-value between 0.6 and 0.8 and optionally separating the extracting agent.

The extracts obtained with such a polar extraction agent, for example with ethanol or an ethanol solution, are surprisingly suitable for stabilization of lipid-rich foodstuffs as compared to extracts which were obtained with extraction agents of lower polarity (such as for example acetone or diethyl ether). This could not be predicted a priori since it is known that polar extraction solvent agents first extract polar contents from the respective material being extracted, and polar substances were generally considered to be unsuitable for the stabilization of lipid-rich foodstuffs on the basis of their low fat solubility.

The grain germ (Poacae,=Graminaceae) extracted in accordance with the invention are preferably wheat, barley or other germ from grains from the subfamily of Pooideae; also corn germ and other germ of the corresponding other grain subfamilies can be employed with good success.

The non-enzymatic browning typically occurs by roasting, and this preferably under the action of dry heat at a temperature of preferably between 50 and 200° C.; roasting temperatures in the range between 120 and 170° C. are preferred and particularly preferred are roasting temperatures of between 140 and 160° C. An increase in the roasting temperature generally brings about, in the mentioned temperature ranges, an improvement in the antioxidative effect of the corresponding extract (see Example 10 below). With an increase in the roasting temperature above 160° C., however, no significant improvement in the antioxidative effect is achieved any longer. At roasting temperatures below approximately 160–170° C. only insignificant amounts—if any—of toxic by-products or minor constituents are formed, while at higher temperatures considerable amounts of these substances could result.

Roasting is preferably carried out for 5–100 minutes.

During browning, products of the Maillard reaction are formed, and it has now been accomplished, by extraction with the mentioned solvents or solvent mixtures, to obtain a corresponding extract which possess a surprisingly high antioxidative effectiveness. Control tests have surprisingly shown that fractionations of this (total) extract do not result in substance compositions which possess an improved antioxidation effectiveness in comparison to the untreated (total) extract, but rather that the obtained (total) extract itself possess the highest effectiveness. This can be traced back to a surprisingly synergistic effect of the extract component substances.

Even though a fractionation does not lead to an improvement in the antioxidative properties of the inventive extract, it is however sometimes useful to separate out the aroma and/or color forming minor constituents of the extract. For this, the person of ordinary skill in the art can use the conventional separation processes.

In accordance with a further aspect, the invention includes in general the use of extracts of non-enzymatically browned grain germ as antioxidative effective agents for stabilization of foodstuffs, in particular lipid-rich foodstuffs or cosmetic agents, wherein for production of the extracts any solvents or solvent mixtures, in particular those which are liquid at room temperature (20–25° C.), can be employed as extraction agents.

However, particularly suitable for use as antioxidants are the extracts in accordance with the invention, in which an extraction agent, particularly from the ethanol including group of the dipolar protic solvent agents, is employed in their production, and in particular one with an $E_T^N$-value between approximately 0.6 (1-propanol) and approximately 0.8 (glycol). These (polar) extracts are surprisingly not inferior to the conventional synthetic antioxidants, and in certain respects are even superior to them.

The invention concerns also foodstuffs and cosmetic agents, which include a stabilizing effective amount of the inventive extract or a fraction of such an extract.

The extracts according to the invention are particularly suitable for stabilizing lipid-rich foodstuffs such as pure conventional plant oils (for example corn oil) or complex, sensitive foodstuffs (such as, for example, unbrowned wheat germ itself). For example, unbrowned wheat germ can be stabilized by roasting a small portion of the wheat germ, extracting the roasted wheat germ with ethanol, and applying the extract to the unbrowned wheat germ.

It has surprisingly however been found within the framework of the invention, that for stabilization of unbrowned grain germ it is not only the inventive extract, but rather also non-enzymatic browned grain germ itself, that can be employed, wherein the unbrowned grain germ is mixed with the non-enzymatically browned grain germ. Herein preferably the ratio of the non-enzymatic browned to the unbrowned grain germ is adjusted to a mass mixing ratio in a range of from 2:100 to 8:100, preferably however from 2:100 to 4:100.

DETAILED DESCRIPTION OF THE INVENTION

Figure 1:
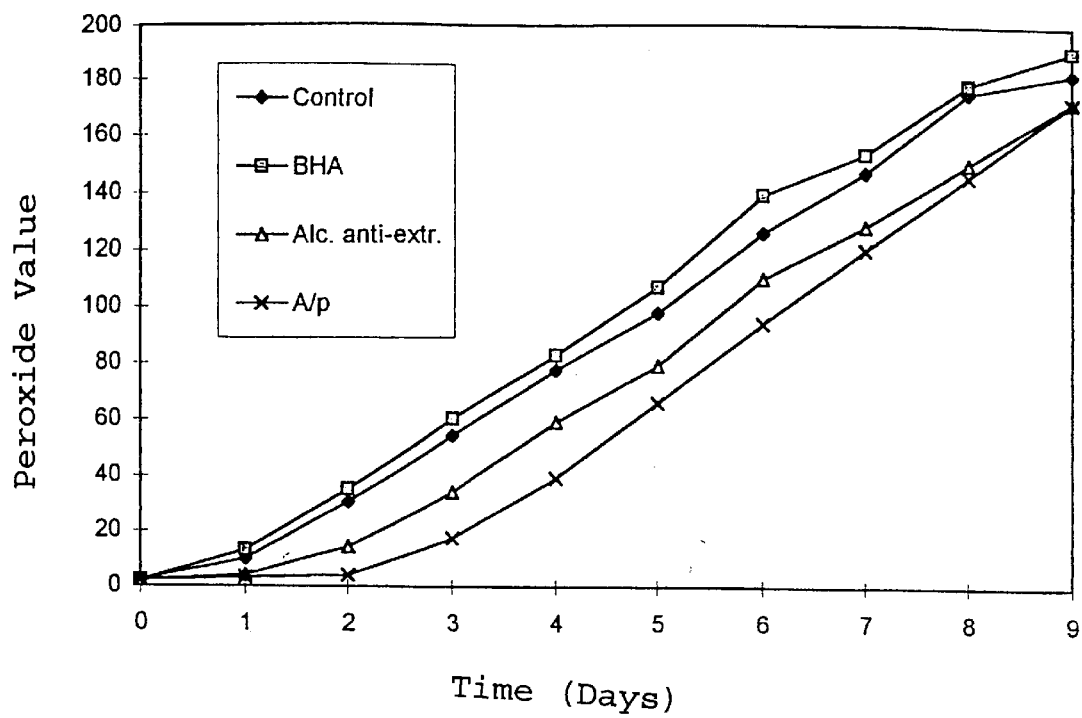
FIG. 1 Peroxide values of conventional wheat germ oil, which was stored at 50° C. with various antioxidants.

In the following the invention will be described in greater detail on the basis of the illustrative embodiments with reference to the figures.

EXAMPLE 1

Definition/Roasting of Wheat Germ

The subject of the following research or, as the case may be, treatment, was three different samples of wheat germ:
a) Fresh wheat germ from a local market.
b) Roasted wheat germ: fresh wheat germ were filled in a 5-ml flask with glass stoppers and maintained for 20 minutes in a metal-block (type S-35-240, from the company Liebisch, Germany) at a temperature of 160° C. Subsequently the thus roasted wheat germ was shock cooled with liquid nitrogen and utilized in the following research.

c) Roasted defatted wheat germ: Fresh wheat germ was defatted, extracted by subjecting for 14–16 hours to a Soxhlet-extraction with n-hexane. Subsequently the thus defatted wheat germ was roasted and further treated as under b).

EXAMPLE 2
Extraction of Roasted Wheat Germ with Various Extraction Solutions

Fresh wheat germ was roasted according to Example 1 b). Respectively 40 g of the obtained roasted wheat germ was cooled, extracted multiple times with a total of 100–300 ml of the extraction solution (a) diethylether, (b) acetone or, as the case may be, (c) ethanol, so that a total of three extracts resulted. Each of these three extracts was concentrated in vacuum at 35° C. using a rotation evaporator, so that the remaining extract volume was 20 ml. Thus 1 ml of extract contained the contents of 2 g roasted wheat germ. Each of the concentrated extracts was quantitatively transferred to a 20 ml-flask and stored in the dark at −30° C. until further use.

Remarks

In the following examples the dosing of antioxidants in the treatment of foodstuffs is given in percentages. Insofar as the dosing data concerns the extract of roasted wheat germ, they are to be understood as follows:

A dosing of for example 10% means that the extract of 10 g wheat germ is added to 100 g foodstuffs (for example wheat germ, corn oil, wheat oil). This corresponds in accordance with the above procedure to an addition of 5 ml concentrated extract.

EXAMPLE 3
Comparison Testing for Stabilization of Wheat Germ Oil with Various Antioxidants 3.1. First a total of 4 samples of respectively 50 g wheat germ oil were subjected to stabilization tests.

For this the samples were filled into open beakers with a diameter of respectively 8.6 cm. Then three of the samples were subjected to various antioxidants with stirring for 10 minutes, and namely with Ascorbylpalmitate (0.02 weight %) as example for an antioxidative effective metal-chelate complex-former, BHA (0.02 weight %) as an example of a phenolic antioxidant or, as the case may be, An inventive ethanol extract according to Example 2c (20%, see remarks for Example 2).

The fourth sample was not supplemented with an antioxidant and served as control.

The samples were stored at 50° C.

3.2. The stabilization test was repeated with otherwise identical conditions, however the storage temperature was 60° C.

The oxidative stability of the various samples (according to 3.1 and 3.2) was determined by repeated analysis, wherein at 24-hour intervals respectively the peroxide value, the concentration of conjugated diene-hydroperoxides and the concentration of α-tocopherol was determined. The peroxide value and the hydroperoxide-concentration thereby served as empirical value for lipid-oxidation.

The results of the measurements are set forth in FIGS. 1–6:

There is shown:

FIG. 1 Peroxide values of conventional wheat germ oil, which was stored at 50° C. with various antioxidants.

Figure 2:
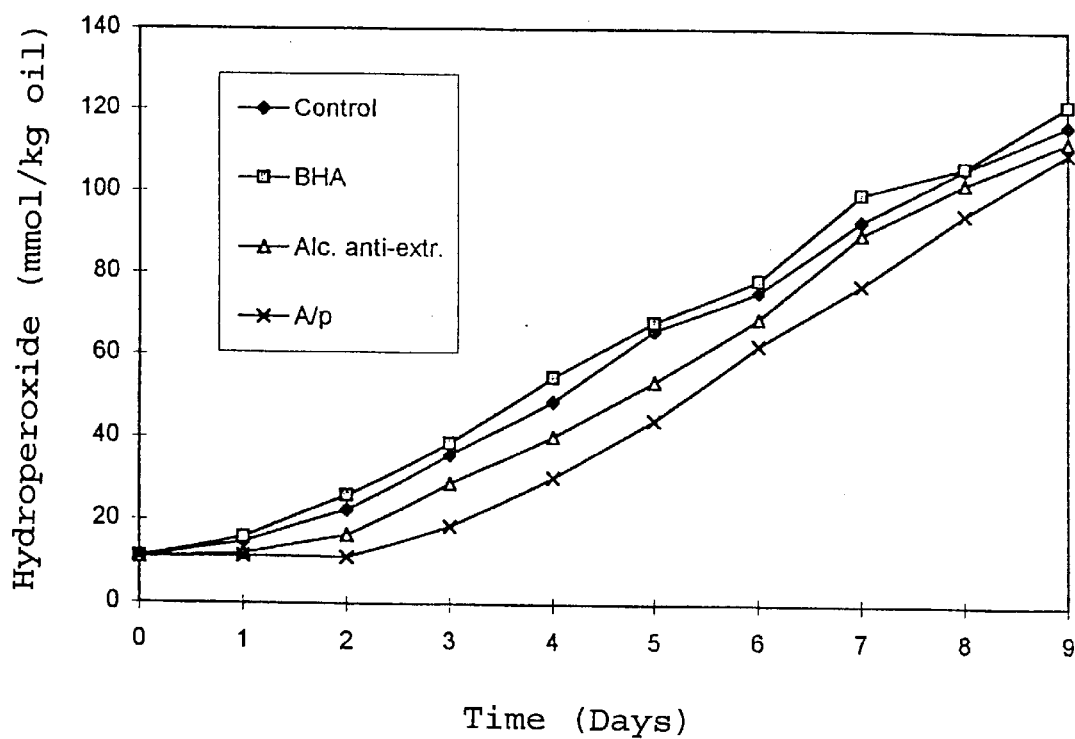
FIG. 2 Concentration of conjugated diene-hydroperoxides in conventional wheat germ oil, which was stored at 50° C. with various antioxidants.

FIG. 2 Concentration of conjugated diene-hydroperoxides in conventional wheat germ oil, which was stored at 50° C. with various antioxidants.

Figure 3:
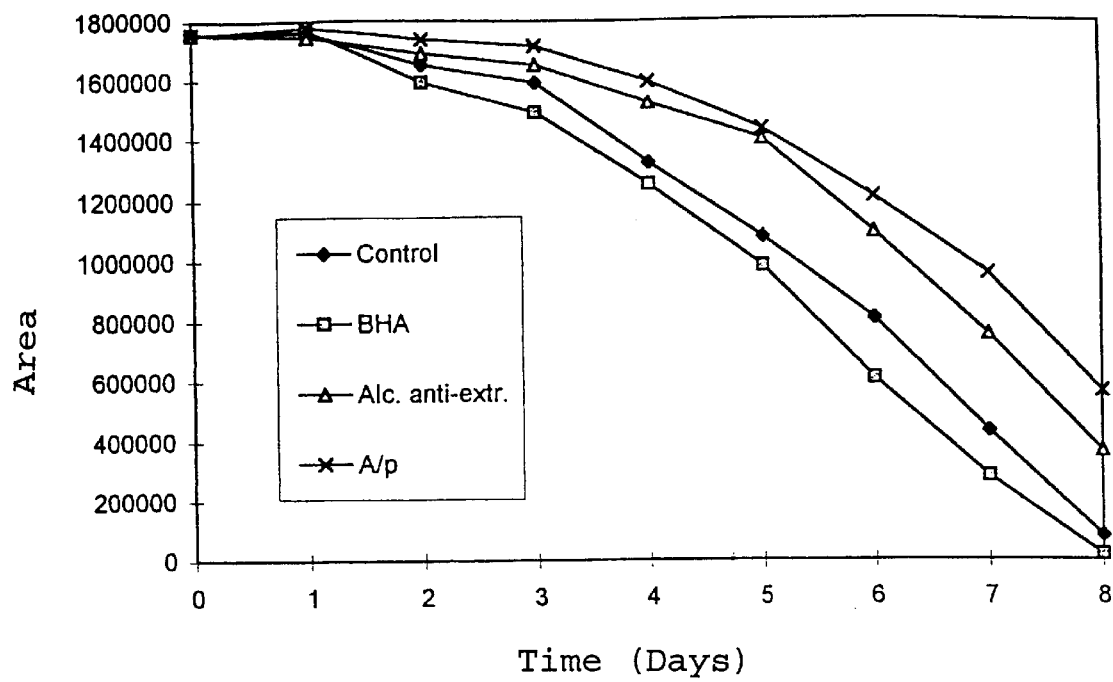
FIG. 3 Concentration of α-tocopherol in conventional wheat germ oil, which was stored at 50° C. with various antioxidants.

FIG. 3 Concentration of α-tocopherol in conventional wheat germ oil, which was stored at 50° C. with various antioxidants.

Figure 4:
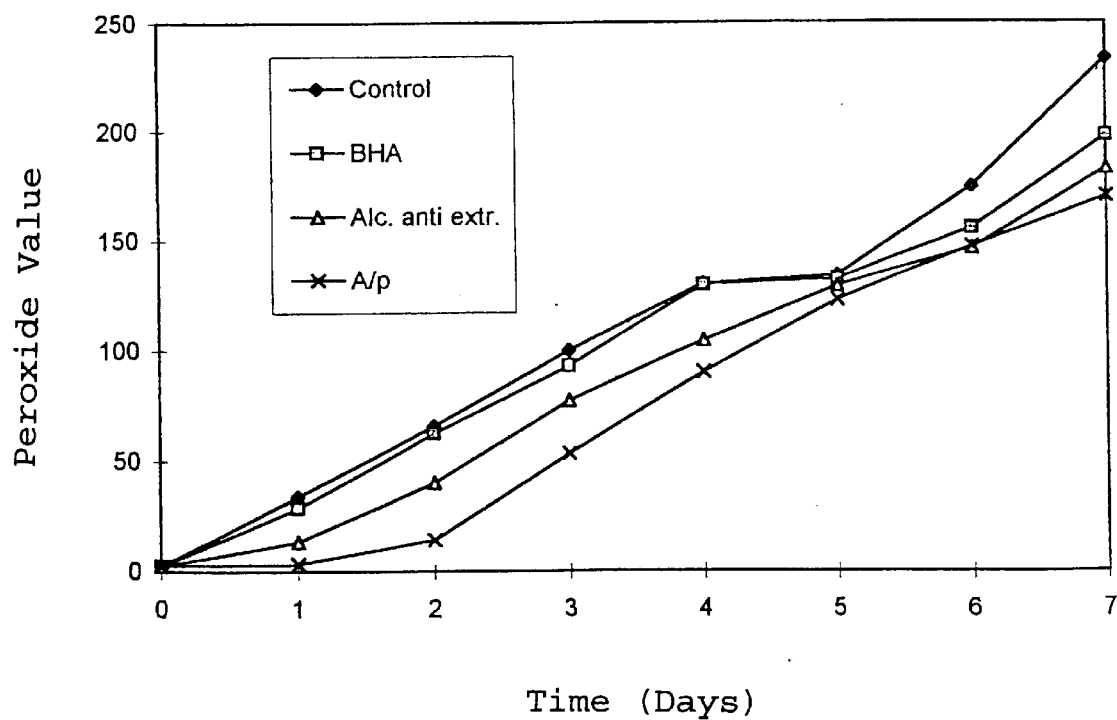
FIG. 4 Peroxide values of conventional wheat germ oil, which was stored at 60° C. with various antioxidants.

FIG. 4 Peroxide values of conventional wheat germ oil, which was stored at 60° C. with various antioxidants.

Figure 5:
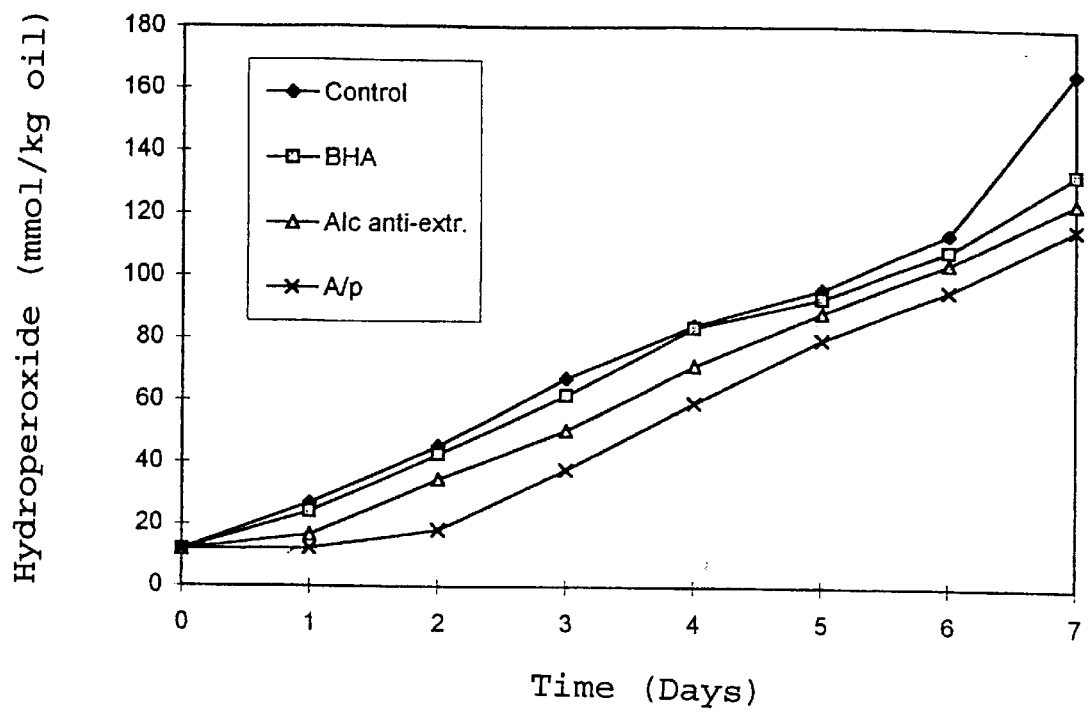
FIG. 5 Concentration of conjugated diene-hydroperoxides in conventional wheat germ oil, which was stored at 60° C. with various antioxidants.

FIG. 5 Concentration of conjugated diene-hydroperoxides in conventional wheat germ oil, which was stored at 60° C. with various antioxidants.

Figure 6:
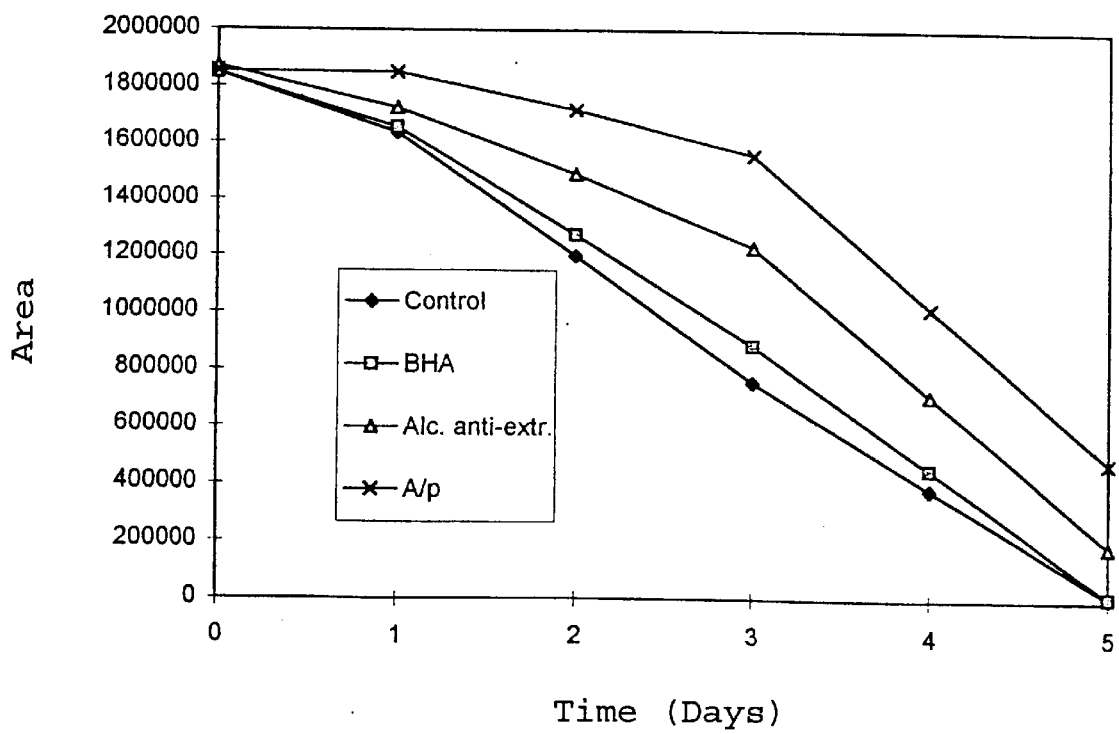
FIG. 6 Concentration of α-tocopherol in conventional wheat germ oil, which was stored at 60° C. with various antioxidants.

FIG. 6 Concentration of α-tocopherol in conventional wheat germ oil, which was stored at 60° C. with various antioxidants.

(Control=Control Sample; BHA=Butyl-hydroxyanisole; Alc. anti-extr.=inventive ethanolic extract according to Example 2c; A/p=Ascorbyl-palmitate)

As can be seen from the comparison of FIGS. 1–3 with FIG. 4–6, the oxidation rate at 60° C. was, as expected, higher than at 50° C., and the induction time at 60° C. was shorter.

The determination of the peroxide-value showed that the 20% ethanolic extract of roasted wheat germ possessed an antioxidative defect which was better than that of BHA, however slightly lower than that of ascorbylpalmitate (see FIG. 1 and 4, in which the increase in the peroxide value correlated to an increase in autooxidation products in wheat germ oil).

The measurements for concentration of conjugated diene-hydroperoxide in wheat germ oil corresponded to the results from the determination of the peroxide-value (see FIG. 2 and 5, in which the increase in the hydroperoxide concentration represented an increase of autooxidation products in wheat germ oil).

The changes in α-tocopherol concentration in wheat germ oil shown in FIG. 3 and 6, which served as an indicator for the stability thereof, likewise confirmed the results of the examination of peroxide-value and for concentration of conjugated diene-hydroperoxide. A reduction in the α-tocopherol concentration is herein to be considered as an analog of an increase in the peroxide value and the concentration of conjugated diene-hydroperoxides.

Rancimat®-measurements confirmed again the results of the series of measurements collected in the figures.

EXAMPLE 4
Comparative Test for Stabilization of Tocopherol-free Corn Oil with Various Antioxidants Four samples of respectively 50 g tocopherol-free corn oil ("stripped corn oil") were tested. These samples were filled into open beakers with a diameter of respectively 8.6 cm. Then three of the samples were supplemented with various antioxidants with stirring for 10 minutes, and namely with ascorbylpalmitate (0.02 weight %), BHA (0.02 weight %) or, as the case may be, an ethanolic extract according to Example 2c (20%). The fourth sample was not supplemented with an antioxidant and served for control purposes.

The samples were stored at 60° C. The oxidative stability of the various samples was determined with repeated analysis wherein at 24-hour intervals respectively the peroxide value and the concentration of conjugated diene-hydroperoxides was determined, see FIGS. 7 and 8.

Figure 7:
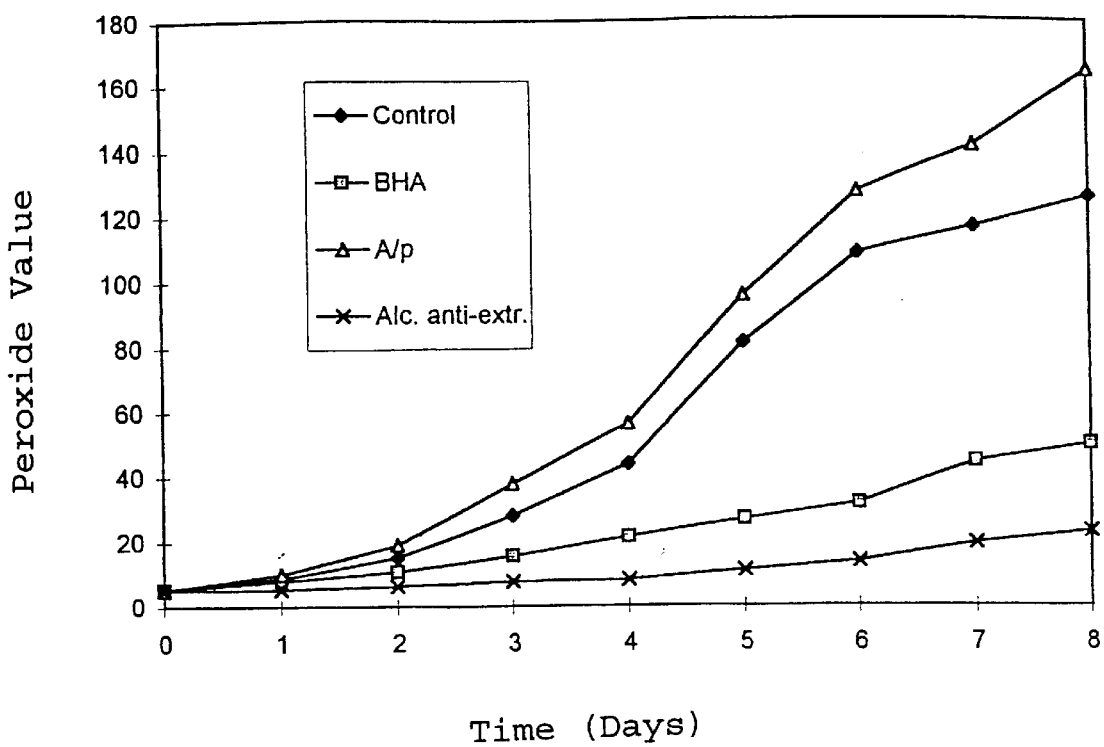
FIG. 7 Peroxide value in tocopherol-free corn oil, which was stored at 60° C. with various antioxidants.

There is shown:

FIG. 7 Peroxide value in tocopherol-free corn oil, which was stored at 60° C. with various antioxidants.

Figure 8:
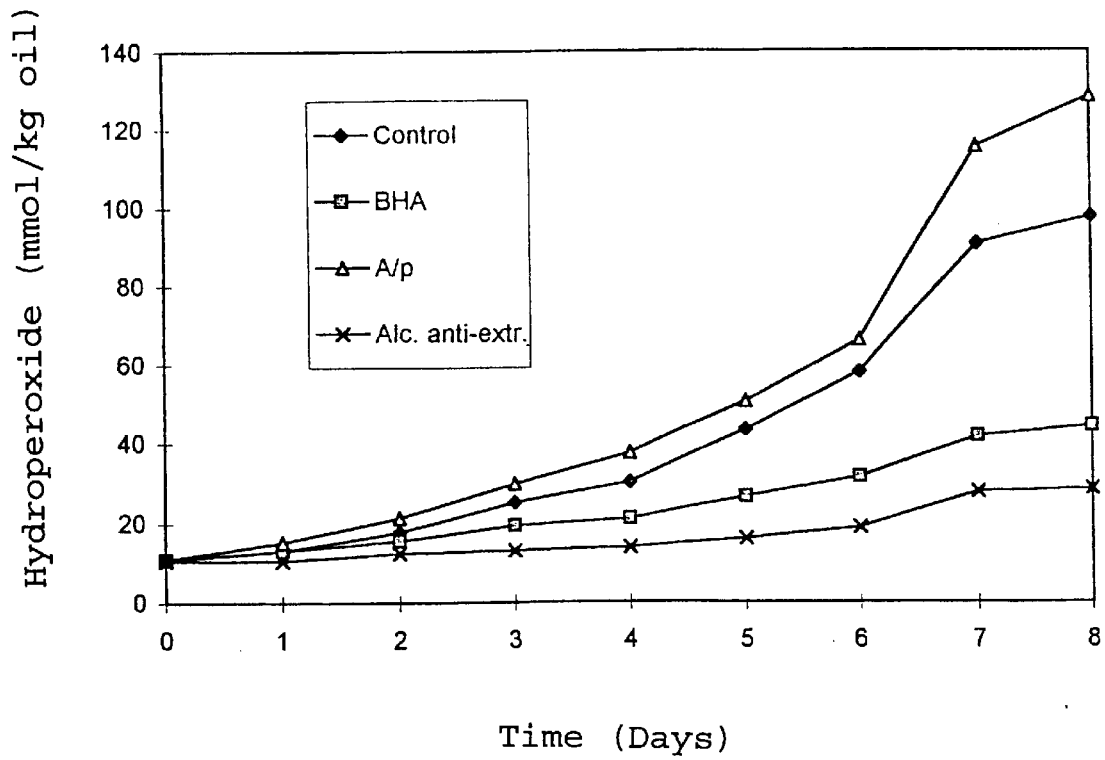
FIG. 8 Concentration of conjugated diene-hydroperoxides in tocopherol-free corn oil, which was stored at 60° C. with various antioxidants.

FIG. 8 Concentration of conjugated diene-hydroperoxides in tocopherol-free corn oil, which was stored at 60° C. with various antioxidants.

(Control=Control Sample: BHA=Butyl-hydroxyanisole; Alc. anti-extr.=inventive ethanolic extract according to Example 2c; A/p=Ascorbyl-palmitate)

Both measurement methods lead to the result, that the antioxidative effect of the 20% ethanolic extract of roasted wheat germ was greater than that of BHA and ascorbylpalmitate. If one considers the results shown in FIG. 8 of hydroperoxide-formation, then it would appear that ascorbylpalmitate (A/p) at a certain concentration level even has a pro-oxidative effect.

EXAMPLE 5

Comparative Test for Stabilization of Wheat Germ with Various Antioxidants

Wheat germ from local markets are as a rule pre-stabilized (treated), in that they are warmed with hot air or hot steam, in order to inactivate the naturally contained enzymes, which otherwise contribute to the spoiling of the wheat germ. Four batches of respectively 500 g of the so pre-stabilized (treated) fresh wheat germ as well as—parallel thereto—four corresponding samples of fresh, untreated wheat germ according to Example 1a) were sprayed with (a) 20 ml ethanol (for control purposes), (b) 20 ml of a 0.01% BHA-solution in ethanol, (c) 20 ml of a 0.01% ascorbylpalmitate-solution in ethanol or, as the case may be, (d) 20 ml of a 8% solution of the ethanolic extract of roasted wheat germ according to Example 2. Each of the eight total batches was spread out into bowls, and namely such that the height of the wheat germ layer in no bowl was higher than 1 cm. The batches were stored at 50° C.

Using a conventional Soxhlet apparatus and with pentane/dichloromethane (2:1) as extraction agent, wheat germ oil samples were extracted in weekly intervals from the batches. The germ oil extracts were filtered, dried for 24 hours over dehydrated sodium sulfate, and then filtered again. The extraction agents were removed under high vacuum at 35° C. The resulting raw oil was directly examined.

The oxidative stability of the wheat germ was analyzed, in that for the obtained oil-samples the peroxide value, the concentration of conjugated diene-hydroperoxide and the concentration of α-tocopherol was determined.

The results represented in FIGS. 9 through 14 show that the ethanolic extract of roasted wheat germ was better suited for stabilization both of treated as well as untreated wheat germ than the conventional antioxidants BHA and ascorbylpalmitate.

Figure 9:
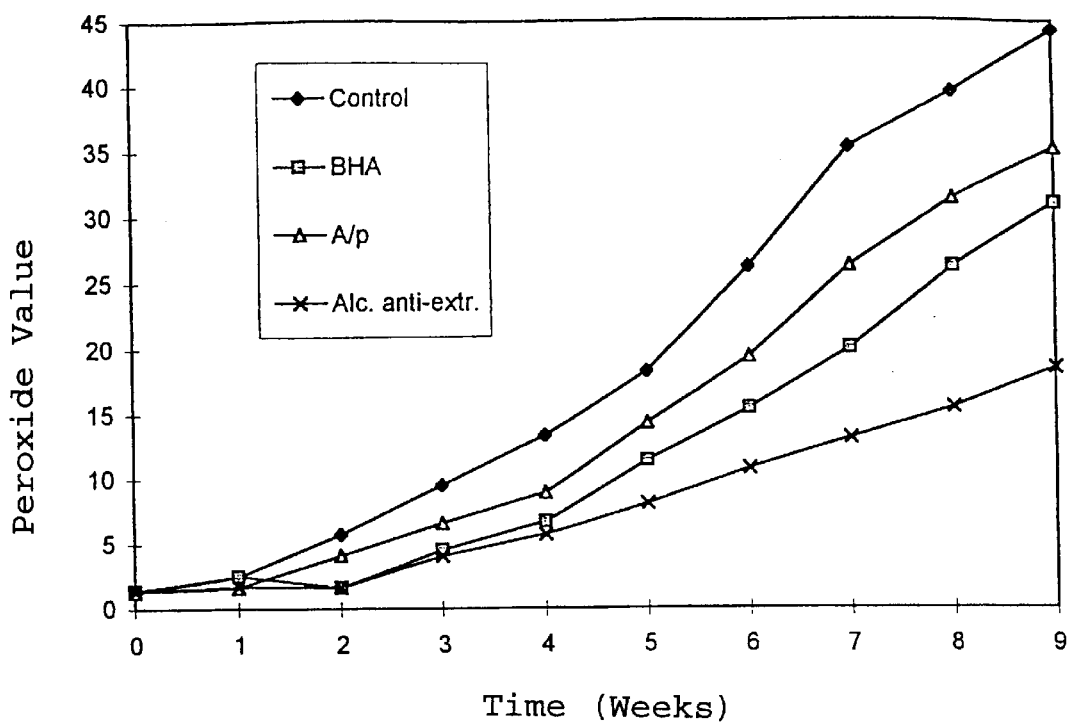
FIG. 9 Peroxide values of treated wheat germ, which was stored at 50° C. with various antioxidants.

There is shown:

FIG. 9 Peroxide values of treated wheat germ, which was stored at 50° C. with various antioxidants.

Figure 10:
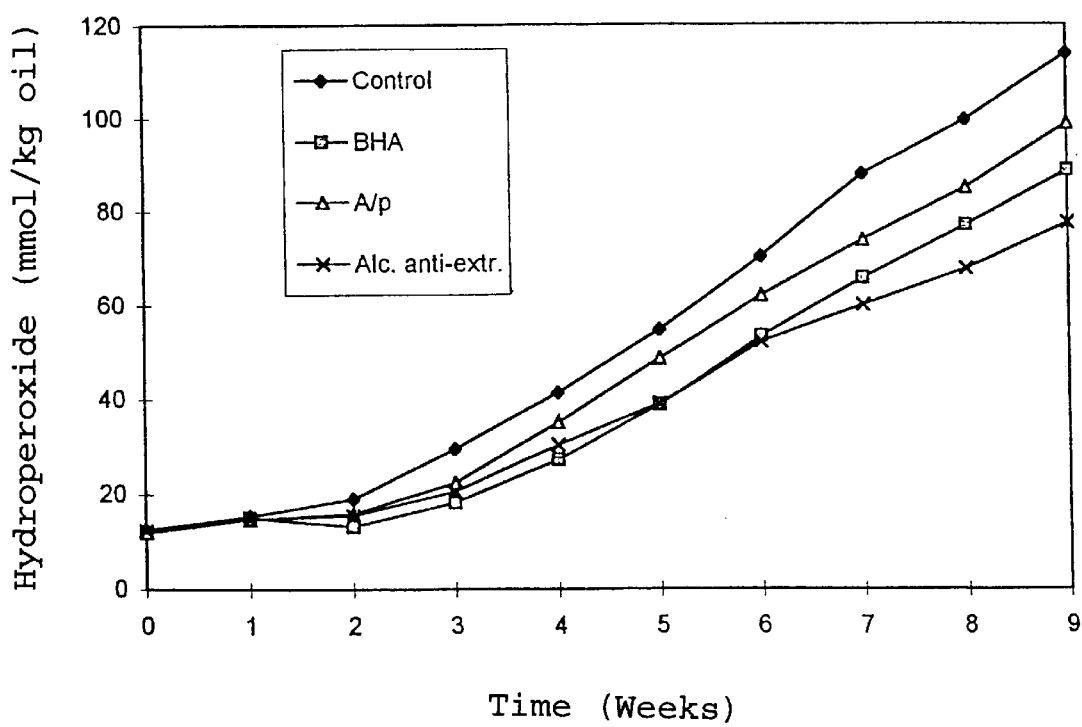
FIG. 10 Concentration of conjugated diene-hydroperoxides in treated wheat germ, which was stored at 50° C. with various antioxidants.

FIG. 10 Concentration of conjugated diene-hydroperoxides in treated wheat germ, which was stored at 50° C. with various antioxidants.

Figure 11:
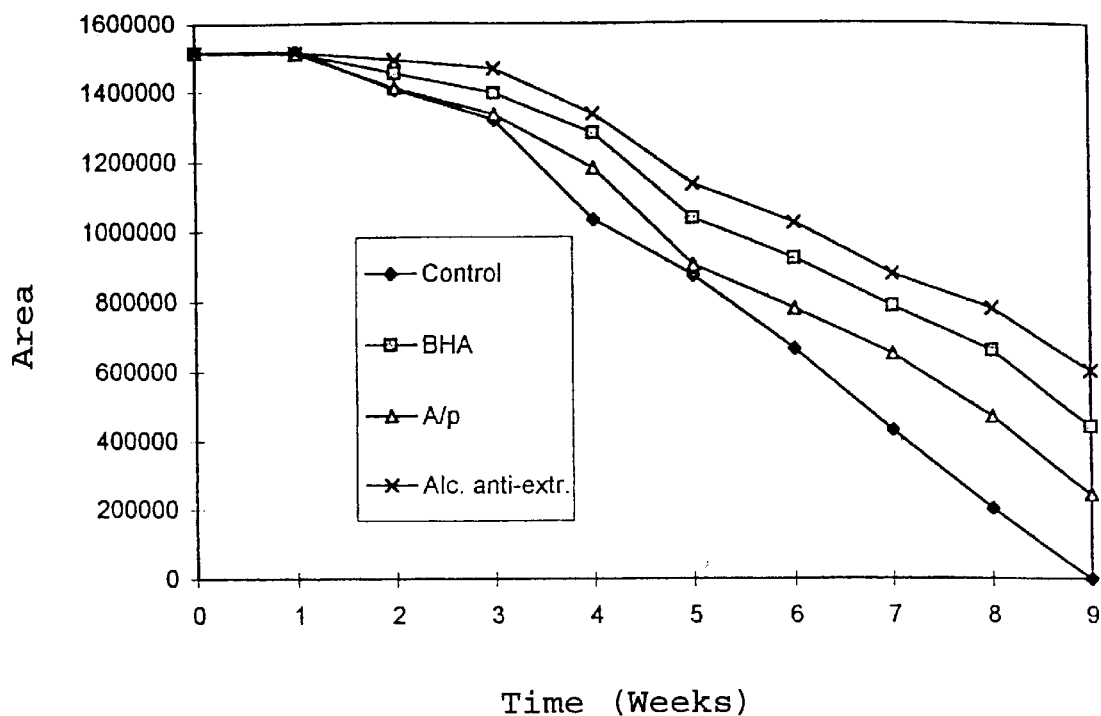
FIG. 11 α-tocopherol concentration in treated wheat germ, which was stored at 50° C. with various antioxidants.

FIG. 11 α-tocopherol concentration in treated wheat germ, which was stored at 50° C. with various antioxidants.

Figure 12:
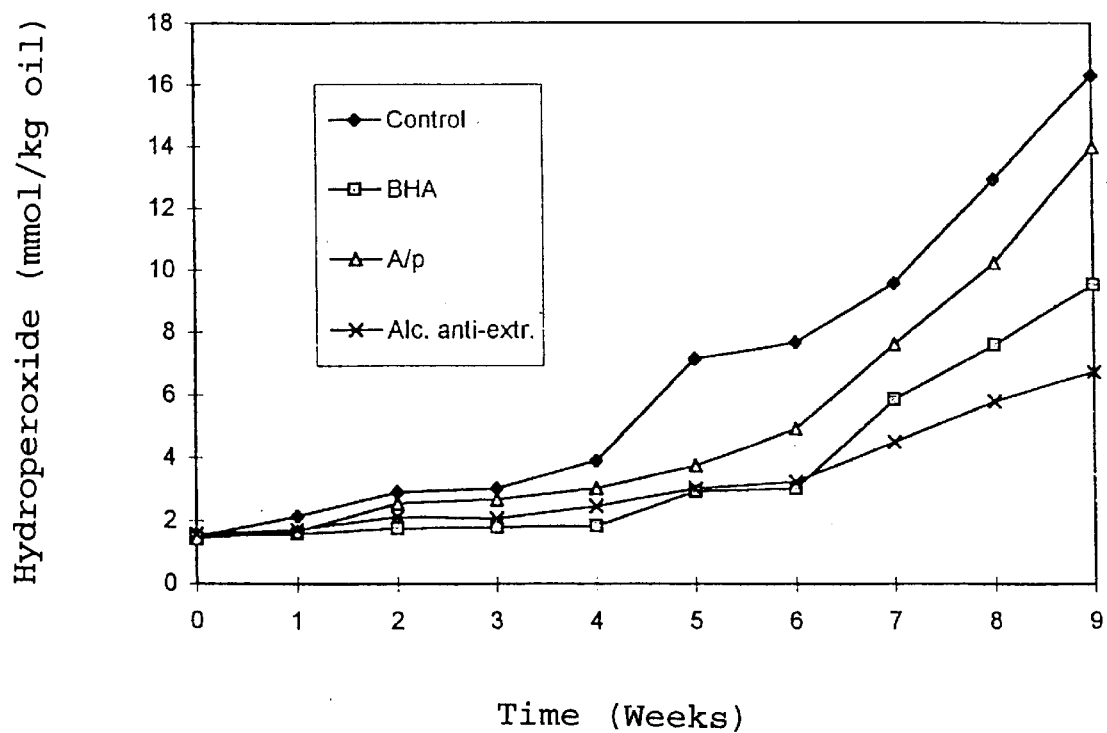
FIG. 12 Peroxide values of untreated wheat germ, which was stored at 50° C. with various antioxidants.

FIG. 12 Peroxide values of untreated wheat germ, which was stored at 50° C. with various antioxidants.

Figure 13:
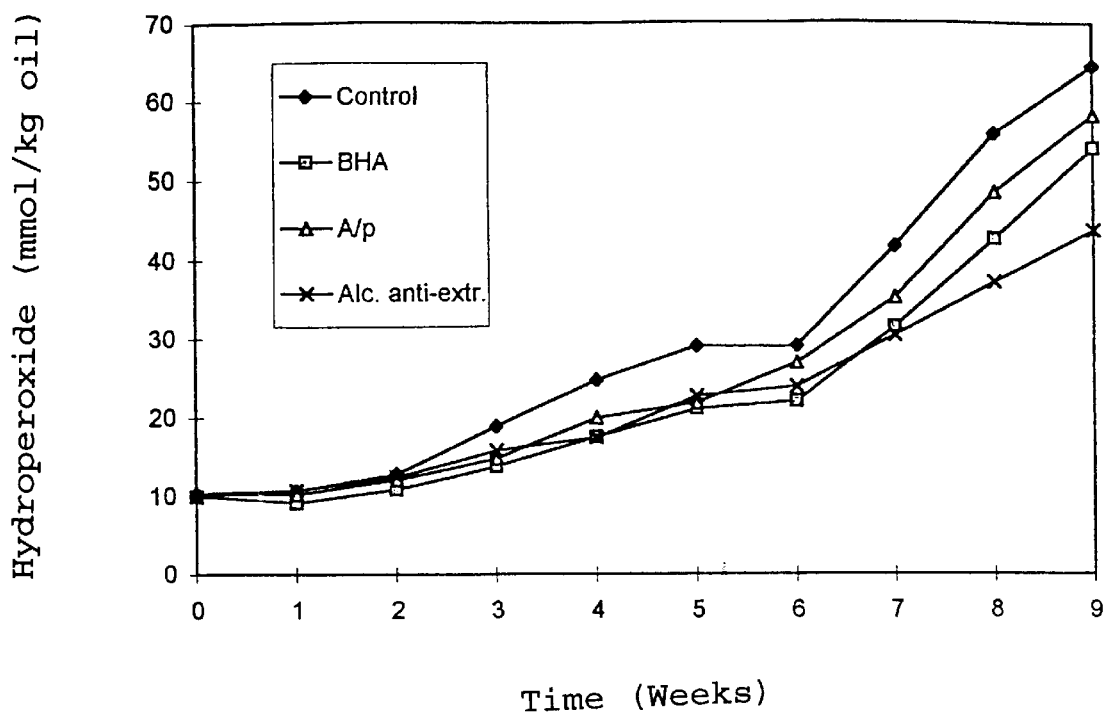
FIG. 13 Concentration of conjugated diene-hydroperoxides in untreated wheat germ, which was stored at 50° C. with various antioxidants.

FIG. 13 Concentration of conjugated diene-hydroperoxides in untreated wheat germ, which was stored at 50° C. with various antioxidants.

Figure 14:
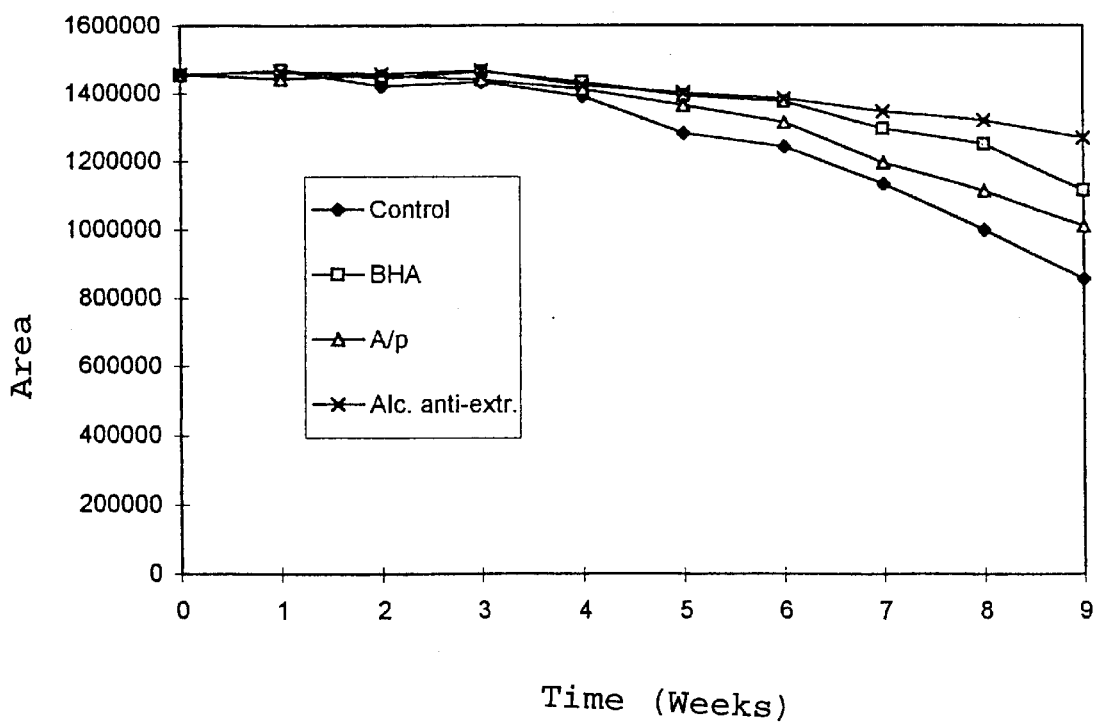
FIG. 14 α-tocopherol concentration in untreated wheat germ, which was stored at 50° C. with various antioxidants.

FIG. 14 α-tocopherol concentration in untreated wheat germ, which was stored at 50° C. with various antioxidants.

(Control=Control Sample: BHA=Butyl-hydroxyanisole; Alc. anti-extr.=inventive ethanolic extract according to Example 2c; A/p=Ascorbyl-palmitate)

EXAMPLE 6

Comparison Test for Stabilization of Corn Oil with Various Extracts of Roasted Wheat Germ Here it is tested whether a difference in oxidative effect of the corresponding extract of roasted wheat germ is achieved with extraction-solution agents of varying polarity. For this the stabilizing effect of extracts of three foodstuff-acceptable extraction-solution agents of various polarity were tested on corn oil (as example of a plant oil), in this at concentration levels of 10% and 20%:

A total of 6 corn oil samples were treated with 10 or as the case may be 20% of a diethylether-acetone or as the case may be ethanol extract of roasted wheat germ; the production of this extract is described in Example 2. The oxidative stability of the samples stored at 60° C. was determined by repeated analysis, wherein at 24-hour intervals respectively the peroxide value, the concentration of conjugated diene-hydroperoxides and the concentration of α-tocopherol was determined.

Figure 15:
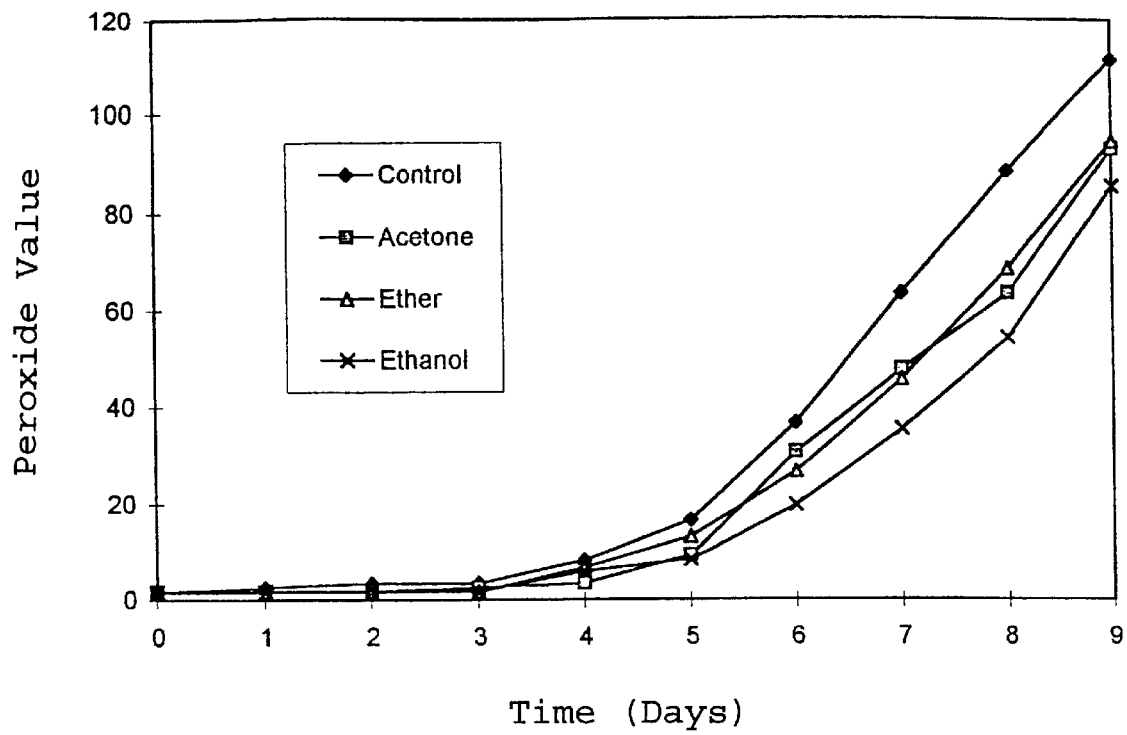
FIG. 15 Peroxide value of corn oil, which was treated with respectively 10% of various solvent agent extracts and stored at 60° C.
Figure 16:
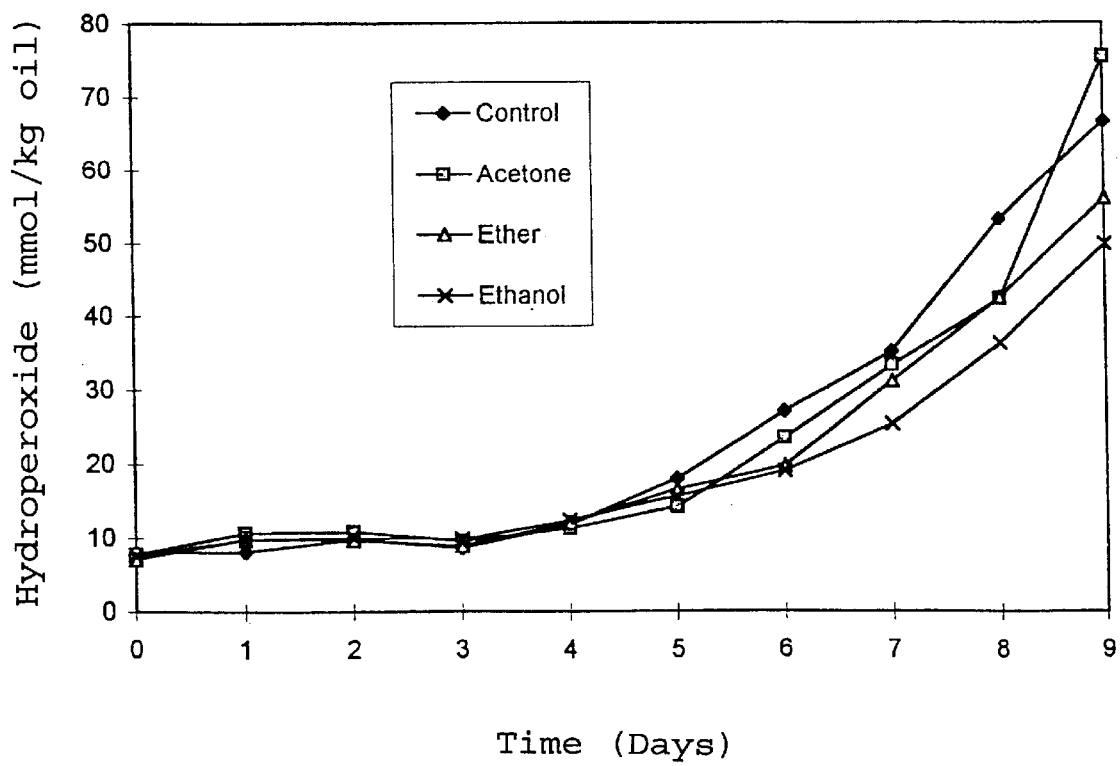
FIG. 16 Concentration of conjugated diene-hydroperoxides in corn oil, which was treated with respectively 10% of various solvent agent extracts and stored at 60° C.
Figure 17:
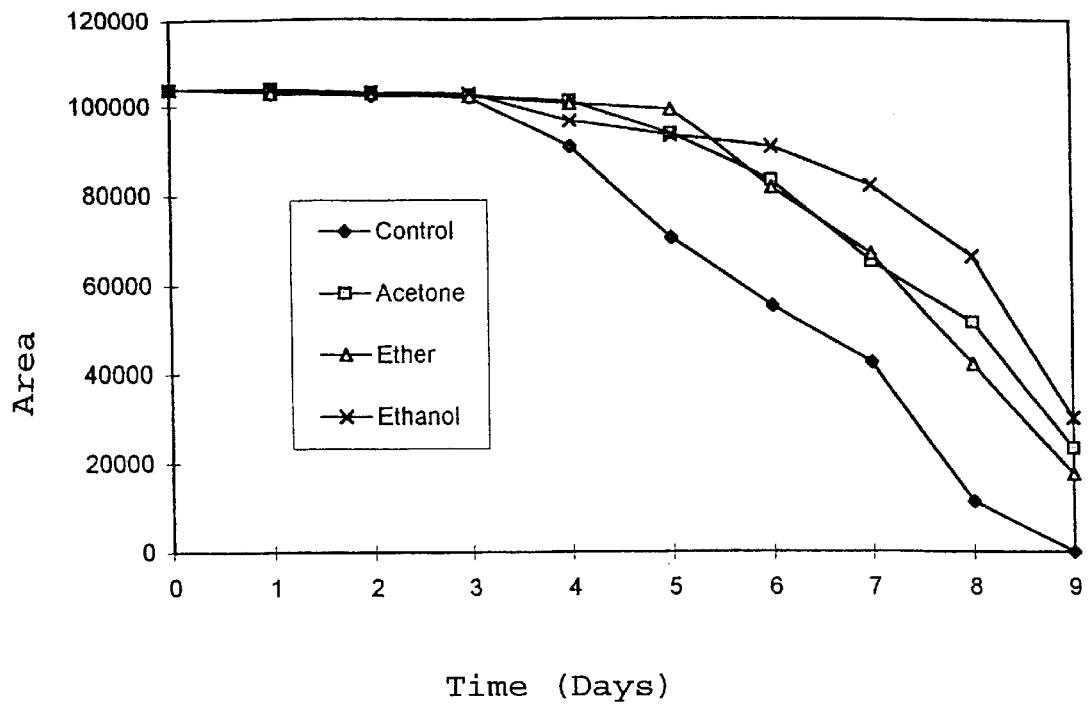
FIG. 17 α-Tocopherol-concentration in corn oil, which was treated with respectively 10% of various solvent agent extracts and stored at 60° C.

At concentration levels of 10% the antioxidative effects of the ether and acetone extracts were similar, however, respectively lower than the antioxidative effect of the ethanolic extract, as can been seen from the following FIGS. 15–17, in which the results of peroxide value, concentration of conjugated diene-hydroperoxides and concentration of tocopherol are indicated.

The clear antioxidative effect of the ethanolic extract of roasted wheat germ is even more distinct at the concentration level of 20%. This can be seen from FIGS. 18–20.

There is shown:

FIG. 15 Peroxide value of corn oil, which was treated with respectively 10% of various solvent agent extracts and stored at 60° C.

FIG. 16 Concentration of conjugated diene-hydroperoxides in corn oil, which was treated with respectively 10% of various solvent agent extracts and stored at 60° C.

FIG. 17 α-Tocopherol-concentration in corn oil, which was treated with respectively 10% of various solvent agent extracts and stored at 60° C.

Figure 18:
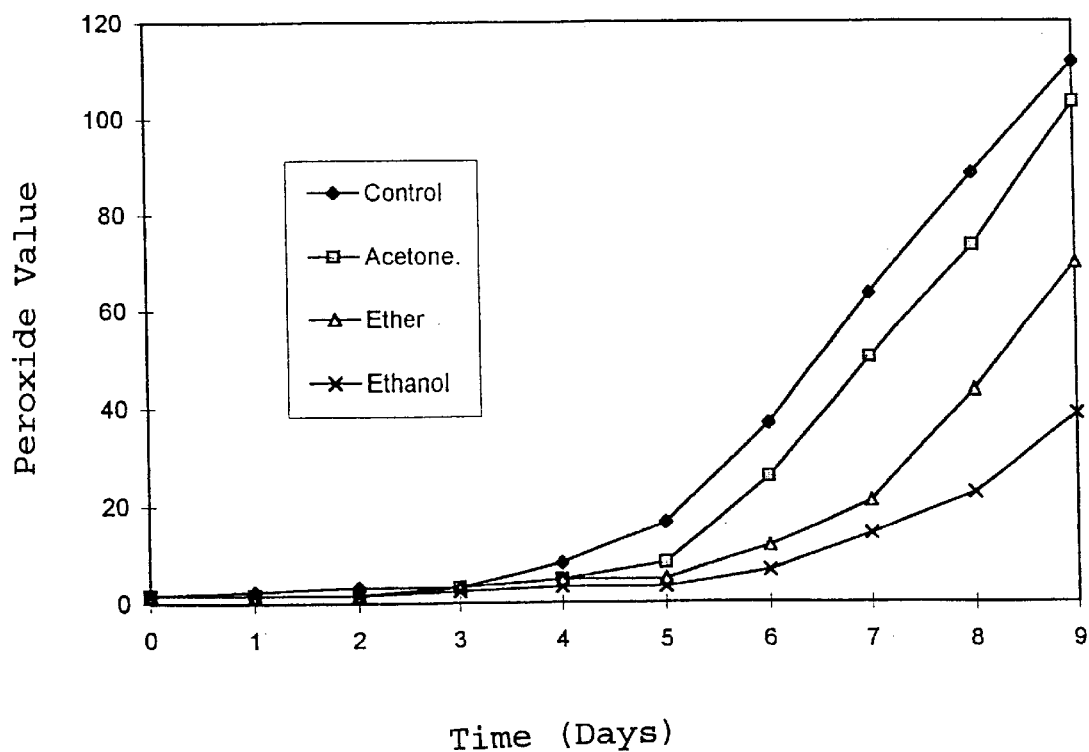
FIG. 18 Peroxide value of corn oil, which was treated with respectively 20% of various solvent agent extracts and stored at 60° C.

FIG. 18 Peroxide value of corn oil, which was treated with respectively 20% of various solvent agent extracts and stored at 60° C.

Figure 19:
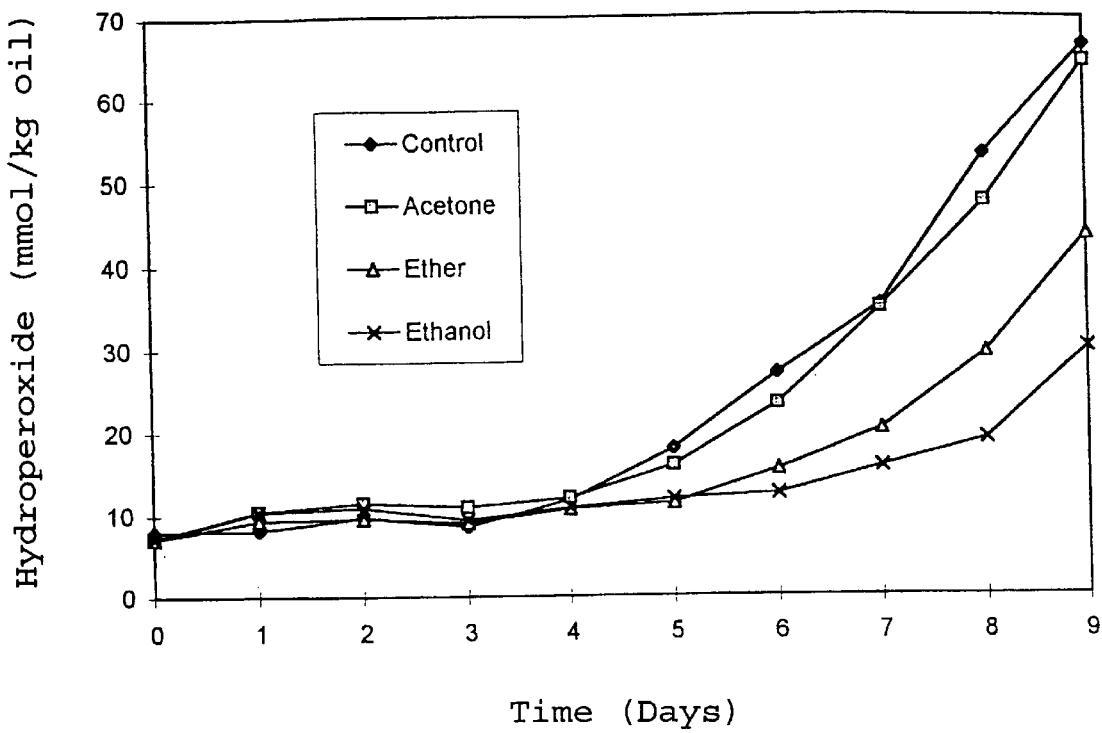
FIG. 19 Concentration of conjugated diene-hydroperoxides in corn oil, which was treated with respectively 20% of various solvent agent extracts and stored at 60° C.

FIG. 19 Concentration of conjugated diene-hydroperoxides in corn oil, which was treated with respectively 20% of various solvent agent extracts and stored at 60° C.

Figure 20:
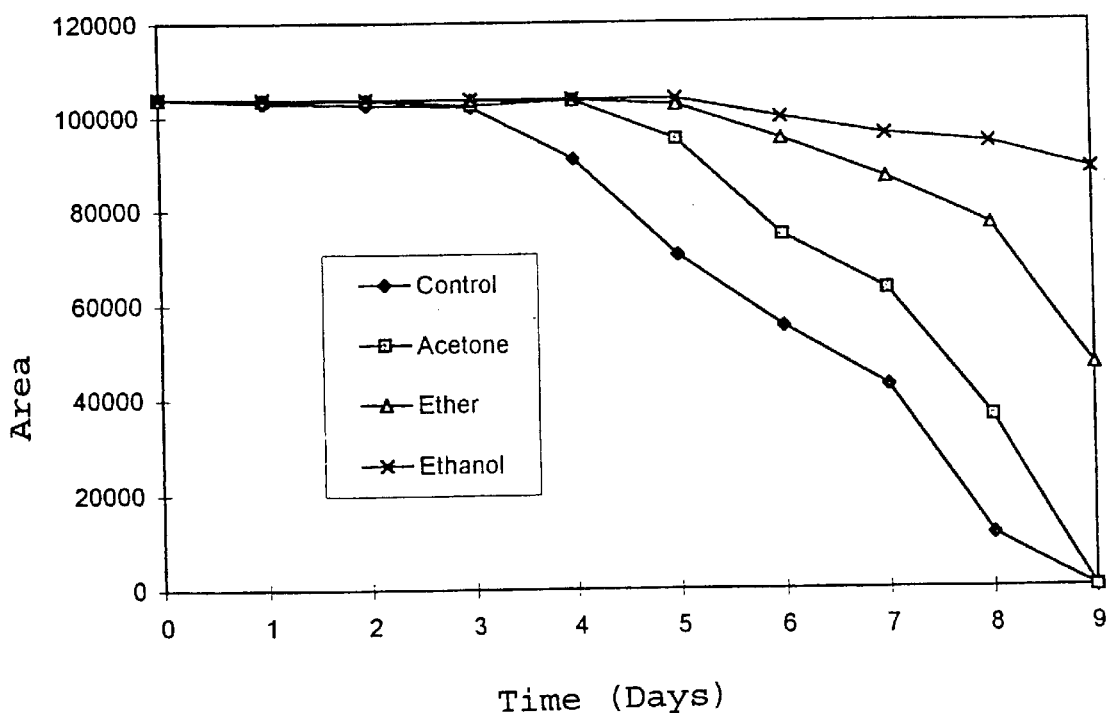
FIG. 20 α-Tocopherol-concentration in corn oil, which was treated with respectively 20% of various solvent agent extracts and stored at 60° C.

FIG. 20 α-Tocopherol-concentration in corn oil, which was treated with respectively 20% of various solvent agent extracts and stored at 60° C.

(Control=Control Sample)

EXAMPLE 7

Test for Stabilization of Untreated Wheat Germ by Mixing with Roasted Wheat Germ Four batches of 500 g of fresh untreated wheat germ were mixed with 0 weight %, 4 weight %, 8 weight %, or, as the case may be, 16 weight % roasted wheat germ.

A further 500 g sample of fresh wheat germ was divided into ten 50 g samples, which were then transferred respectively to a petri dish of 19 cm diameter and were subjected to microwave treatment at 600 watt for 5 minutes. The ten 50 g samples were then again recombined.

Each of the thus 5 total samples of 500 g was spread out in 2 bowls and stored at 50° C.

Figure 21:
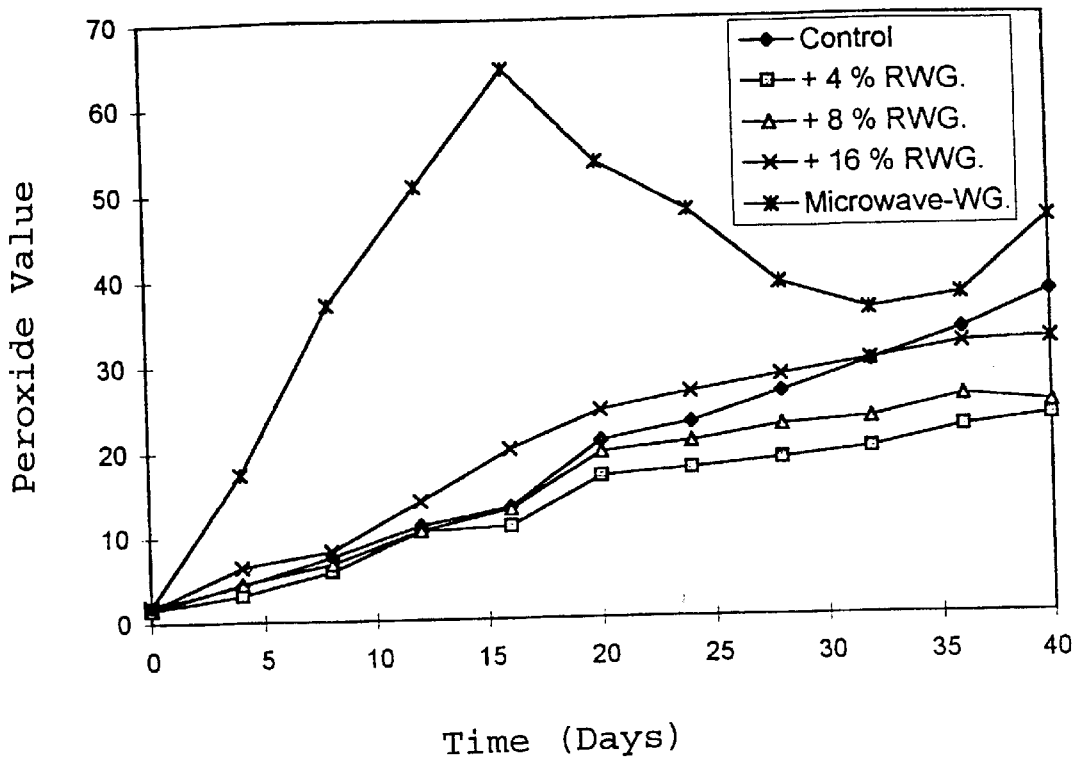
FIG. 21 Peroxide value of wheat germ, which was stored at 50° C. with various concentrations of roasted wheat germ.
Figure 22:
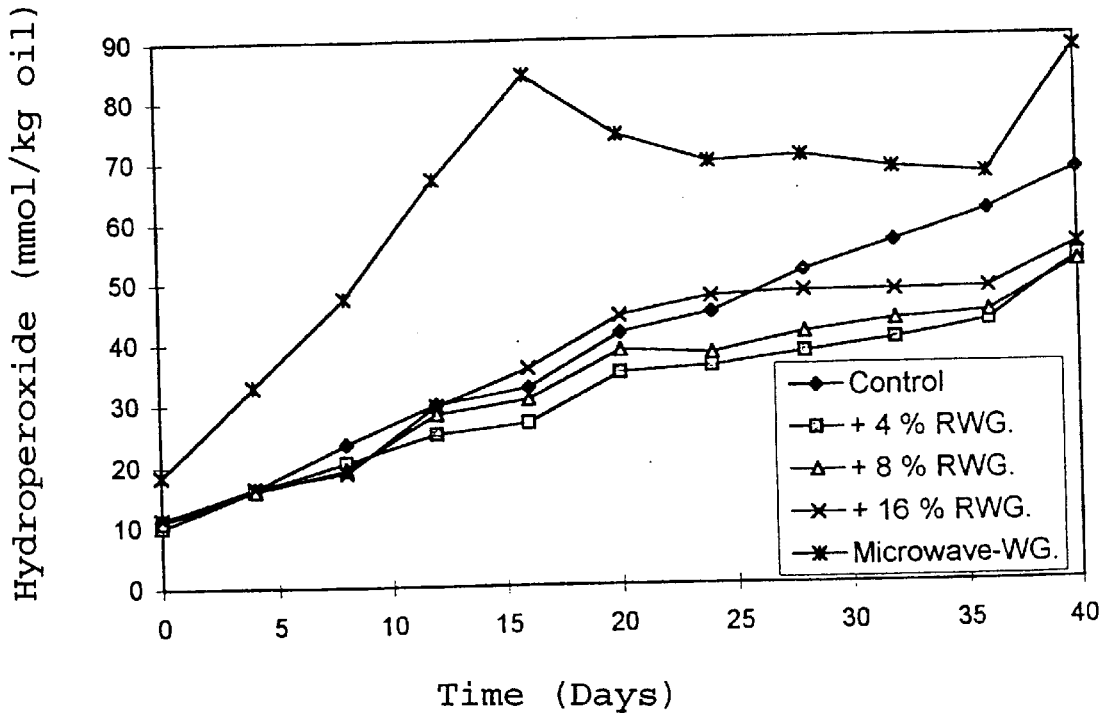
FIG. 22 Concentration of conjugated diene-hydroperoxide in wheat germ, which was stored at 50° C. with various concentrations of roasted wheat germ.
Figure 23:
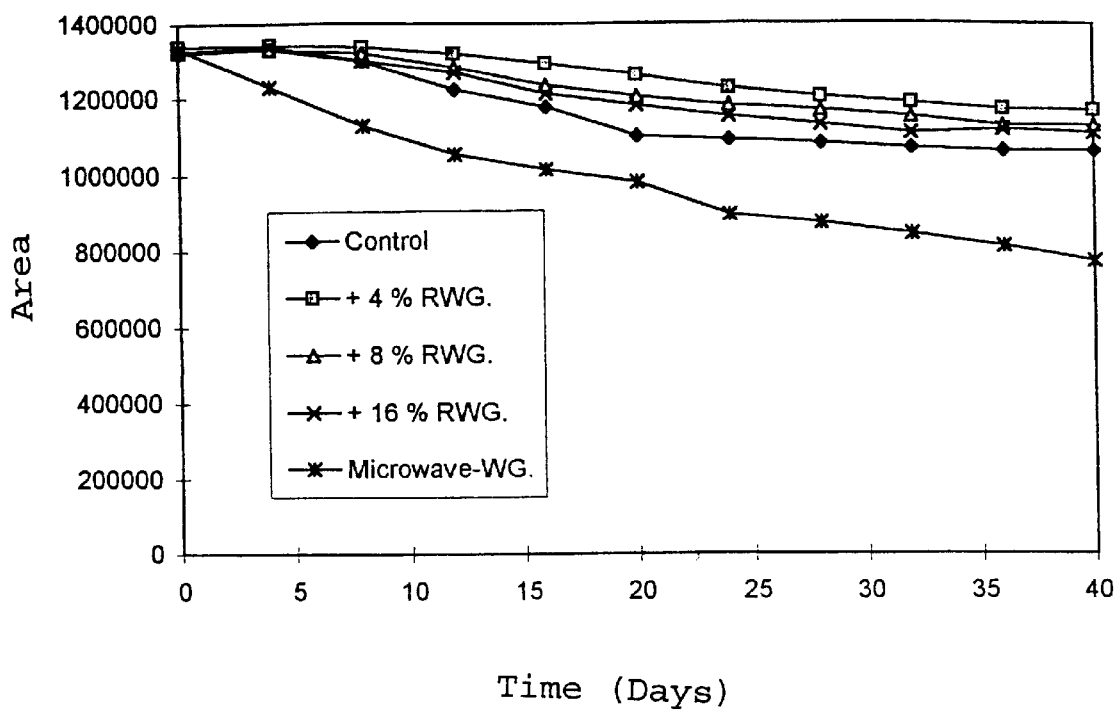
FIG. 23 α-Tocopherol-concentration in wheat germ, which was stored at 50° C. with various concentrations of roasted wheat germ.

The oxidative stability of the samples was determined by repeated analysis, wherein at 24-hour intervals respectively the peroxide value, the concentration of conjugated diene-hydroperoxides and the concentration of α-tocopherol was determined, see FIGS. 21–23.

The stabilization of wheat germ by addition of small amounts of roasted wheat germ was more effective than a microwave treatment, which is conventionally employed to stabilize the lipolytic enzyme of the germ. The addition of 4% roasted wheat germ had better antioxidative effect at 50° C. than the addition of 8% or 16% roasted wheat germ. At addition of 16% roasted wheat germ, a prooxidative effect was discovered as a matter of fact in the first 30 days.

The test was repeated with a further group of samples, wherein respectively 500 g fresh untreated wheat germ was mixed with 8 weight %, 2 weight %, 4 weight %, 6 weight % or, as the case may be, 8 weight % roasted wheat germ. With otherwise identical tests and evaluation conditions, the samples were stored however at 40° C.

Figure 24:
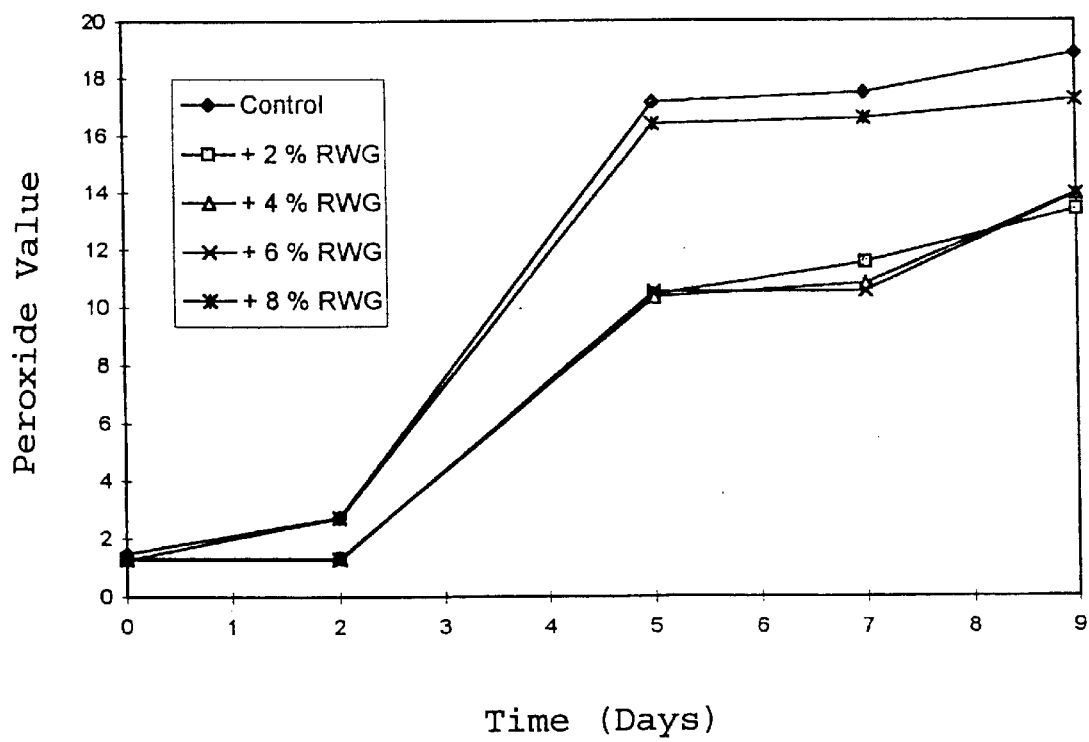
FIG. 24 Peroxide value of wheat germ, which was stored at 40° C. with various concentrations of roasted wheat germ.
Figure 25:
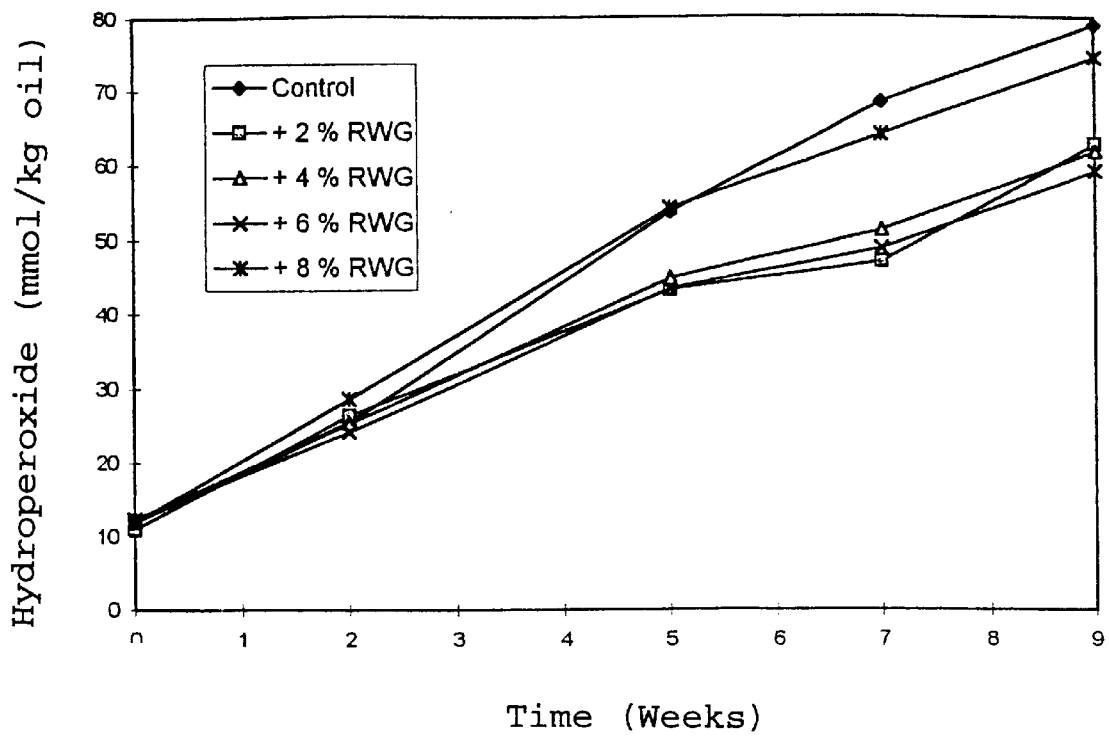
FIG. 25 Concentration of conjugated diene-hydroperoxide in wheat germ, which was stored at 40° C. with various concentrations of roasted wheat germ.
Figure 26:
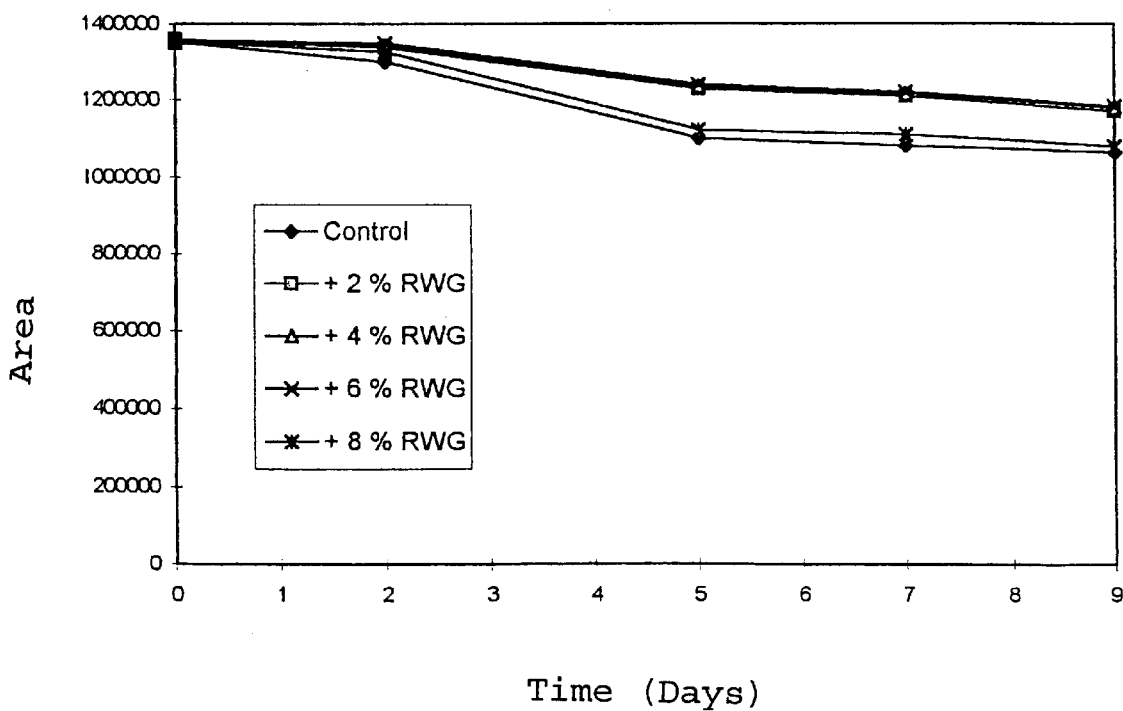
FIG. 26 α-Tocopherol-concentration in wheat germ, which was stored at 40° C. with various concentrations of roasted wheat germ.

As can be seen from FIGS. 24–26, the addition of 2%, 4% and 6% roasted wheat germ had an approximately equal stabilizing effect on the fresh wheat germ at a storage temperature of 40° C. At addition of 8% roasted wheat germ the antioxidative effect was however no longer so distinct as with the lower concentrations.

There is shown:

FIG. 21 Peroxide value of wheat germ, which was stored at 50° C. with various concentrations of roasted wheat germ.

FIG. 22 Concentration of conjugated diene-hydroperoxide in wheat germ, which was stored at 50° C. with various concentrations of roasted wheat germ.

FIG. 23 α-Tocopherol-concentration in wheat germ, which was stored at 50° C. with various concentrations of roasted wheat germ.

FIG. 24 Peroxide value of wheat germ, which was stored at 40° C. with various concentrations of roasted wheat germ.

FIG. 25 Concentration of conjugated diene-hydroperoxide in wheat germ, which was stored at 40° C. with various concentrations of roasted wheat germ.

FIG. 26 α-Tocopherol-concentration in wheat germ, which was stored at 40° C. with various concentrations of roasted wheat germ.

(RWG=roasted wheat germ; microwave-WG=microwave treated wheat germ)

EXAMPLE 8

Preparative HPLC-Fractionation of the Ethanolic Extract of Roasted, Fresh or, as the Case may be, Defatted Wheat Germ Two ethanolic extracts of roasted wheat germ were produced.

The first ethanolic extract originated from roasted fresh wheat germ according to Example 1 b; the second ethanolic extract originated from roasted, defatted wheat germ according to Example 1 c.

These two extracts were fractionated using preparative HPLC under use of a diol-column (Lichrosorb, 250×25 ml, particle size 7 μm, Merck, Darmstadt, Germany). The elution system was respectively dichloromethane (I) and methanol (II). The gradient was respectively 100% I for 10 minutes and was then brought up to 50% II by linear increase of the proportion II up to the $100^{th}$ minute; after further 10 minutes it was respectively increased to 100% II. At these gradients the system was maintained up to the $130^{th}$ minute. The flow-through rate was 10 ml $min^{-1}$, and the injection volume was 2 l.

The respective eluate was collected in a fraction collector. A total of six fractions were obtained, and namely one fraction for the time interval from 0–32 minutes (1), 32–44 minutes (2), 44–56 minutes (3), 56–76 minutes (4), 76–86 minutes (5) and 86–130 minutes (6). The fractions were concentrated in a vacuum at 40° C. and quantitatively transferred to a 5 ml measuring flask. It was respectively filled as much as possible with ethanol. The fractions were stored at −30° C. until they were used in the comparative testing in Example 9.

EXAMPLE 9

Comparison of Antioxidative Effect of the Fractions from the Fractionation According to Example 8

Four ethanolic fractions according to Example 8 were tested for their stabilizing properties. Corn oil was employed as the foodstuff to be stabilized, and namely on the one hand tocopherol-free corn oil and on the other hand corn oil with a natural component of tocopherol.

1. First, samples of respectively 10 g tocopherol-free corn oil ("stripped corn oil") were employed. To these samples was added respectively 2.5 ml from one of the 6 fractions of the ethanolic extract of roasted fresh wheat germ or, as the case may be, roasted defatted wheat germ. For control purposes a 1 ml sample of the original ethanolic extract of roasted wheat germ (either fresh, that is, fat containing, or defatted) was treated with 1.5 ml ethanol, and a further control sample contained 2.5 ml ethanol. The samples were respectively stirred for 10 minutes.

Subsequently the samples were stored at 60° C.

The oxidative stability was determined by repeated analysis, wherein at 24 hour intervals respectively the concentration of conjugated diene-hydroperoxide was determined.

2. The comparison test was repeated with tocopherol-containing corn oil, in order also to test insofar the stability of the fractions.

The results of the tests are collectively represented in FIGS. 27–30.

Figure 27:
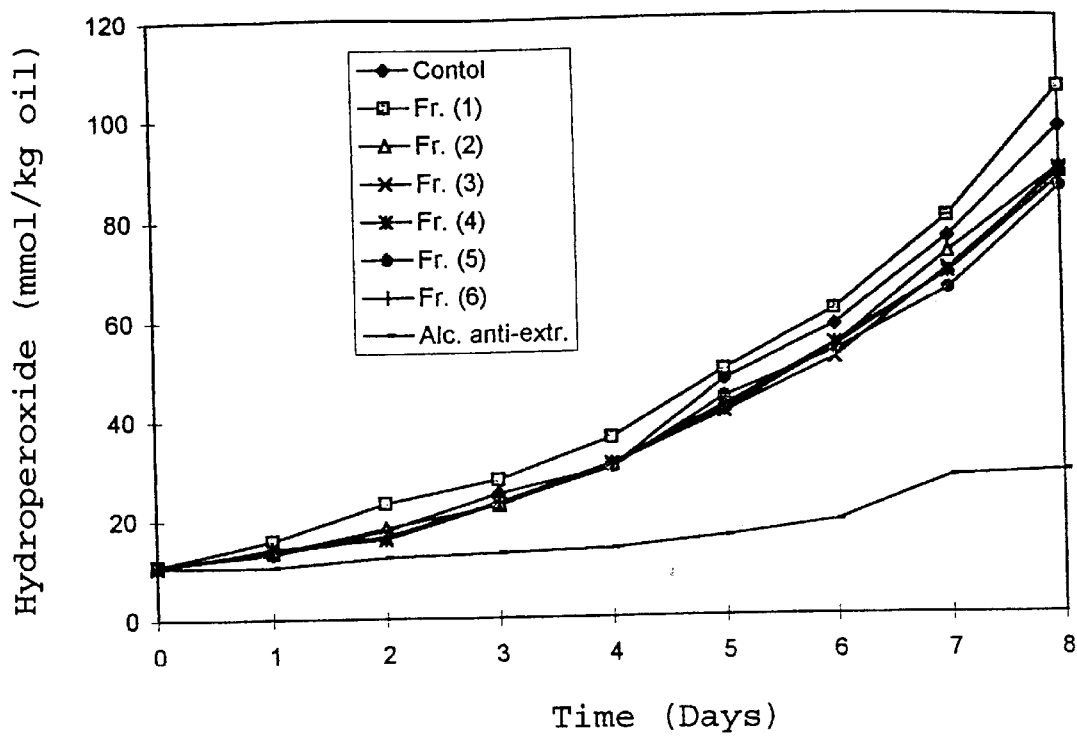
FIG. 27 Concentration of conjugated diene-hydroperoxides in tocopherol-free corn oil, which was treated with fractions 1–6 from the ethanolic extract of roasted, fresh wheat germ and stored at 60° C.

There is shown:

FIG. 27 Concentration of conjugated diene-hydroperoxides in tocopherol-free corn oil, which was treated with fractions 1–6 from the ethanolic extract of roasted, fresh wheat germ and stored at 60° C.

Figure 28:
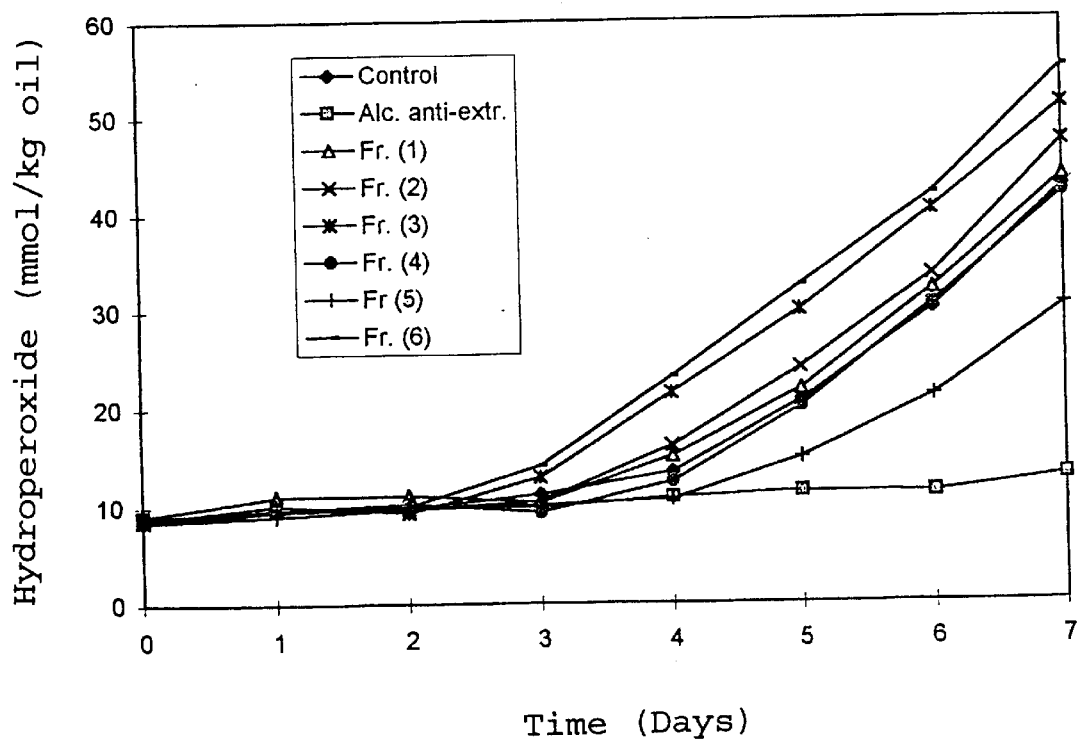
FIG. 28 Concentration of conjugated diene-hydroperoxides in tocopherol containing corn oil, which was treated with fractions 1–6 from the ethanolic extract of roasted, fresh wheat germ and stored at 60° C.

FIG. 28 Concentration of conjugated diene-hydroperoxides in tocopherol containing corn oil, which was treated with fractions 1–6 from the ethanolic extract of roasted, fresh wheat germ and stored at 60° C.

Figure 29:
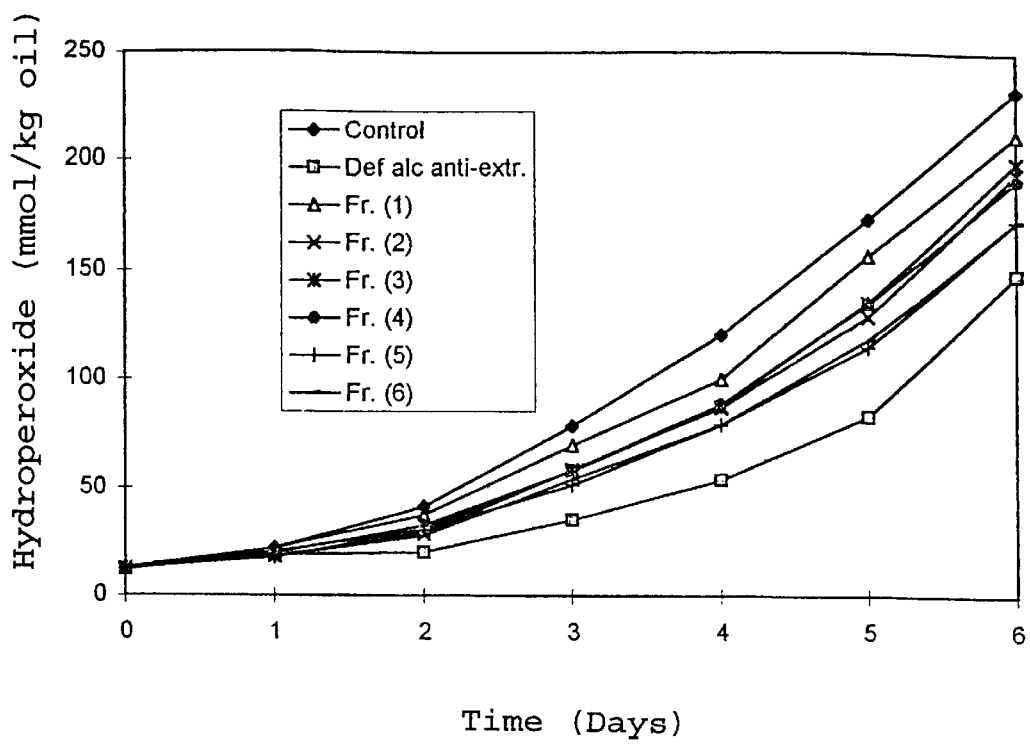
FIG. 29 Concentration of conjugated diene-hydroperoxides in tocopherol-free corn oil, which was treated with fractions 1–6 from the ethanolic extract of roasted, defatted wheat germ and stored at 60° C.

FIG. 29 Concentration of conjugated diene-hydroperoxides in tocopherol-free corn oil, which was treated with fractions 1–6 from the ethanolic extract of roasted, defatted wheat germ and stored at 60° C.

Figure 30:
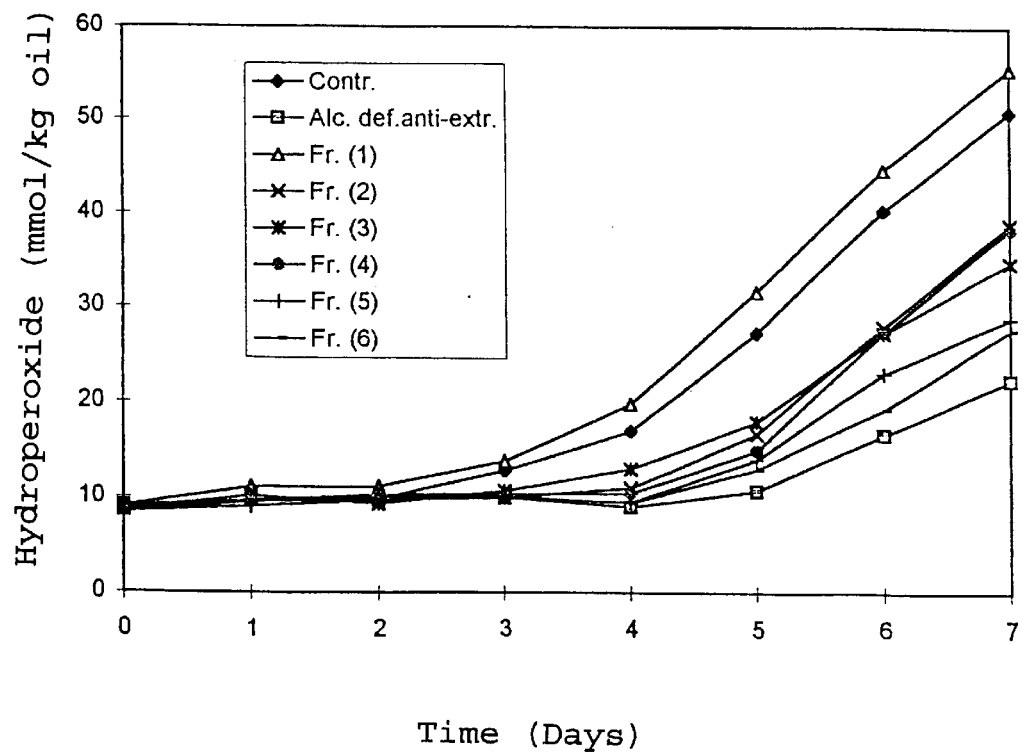
FIG. 30 Concentration of conjugated diene-hydroperoxides in tocopherol containing corn oil, which was treated with fractions 1–6 from the ethanolic extract of roasted, defatted wheat germ and stored at 60° C.

FIG. 30 Concentration of conjugated diene-hydroperoxides in tocopherol containing corn oil, which was treated with fractions 1–6 from the ethanolic extract of roasted, defatted wheat germ and stored at 60° C.

(Fr.=fractions; Alc. anti-extr=ethanolic extract of fresh wheat germ; Def alc anti-extr=ethanolic extract of defatted wheat germ)

The experiments showed first that the antioxidative effect of the respective total extract of fresh or defatted wheat germ was better than the effect of the individual fractions, see FIGS. 27–30.

In the comparison of the extracts of fresh and defatted wheat germ, surprisingly the extract of fresh (that is fat containing) wheat germ proved itself to be more effective; this can be seen by the side by side comparison of the FIGS. 27 and 29 as well as the side by side comparison of FIGS. 28 and 30.

These results are possibly based upon a synergistic effect between the various constituent compounds of the raw extract of fresh wheat germ.

It was further determined, that the differences in the antioxidative effect between the respective 6 fractions (fresh or fat-free) during testing with use of tocopherol-free corn oil was very small, see FIGS. 27 and 29.

In the test using corn oil which contained tocopherol, fractions 5 (both fat containing as well as defatted) and 6 (defatted) showed the highest antioxidative effectiveness within the tested fractions, see FIGS. 28 and 30. The differences between the fractions were (in comparison with the of tocopherol-free corn oil) generally higher, see FIGS. 27–30.

EXAMPLE 10

Comparison Test for Experimentation of the Influence of the Roasting Temperature upon the Antioxidative Effect of Extracted Wheat Germ Extract in the Treatment of Tocopherol-free Corn Oil Analogously to the production of roasted wheat germ according to Example 1 b) fresh wheat germ was filled into a 5-ml flask with glass stopper and maintained for 20 minutes in a metallblock (Type S-35-240, produced by the company Liebisch, Germany) at a temperature at a) 140° C.
b) 160° C.
c) 180° C. and
d) 200° C.

Subsequently the wheat germ roasted at different temperatures were shock cooled with liquid nitrogen.

Respectively 40 g of the wheat germ produced by the different roasting temperatures according to a)–d) were (analogous to Example 2 c)) extracted multiple times with ethanol, so that a total of four extracts resulted. Each of these four extracts was concentrated using a rotation evaporator at 35° C. in vacuum, so that the remaining extract volume was 20 ml. Each 1 ml extract thus contained the content substances of 2 g roasted wheat germ. Each of the four concentrated extracts was quantitatively transferred to a 20 ml flask and stored at −30° C. in the dark until further use.

Analogously to Example 4, 5 samples of respectively 50 g tocopherol-free corn oil ("stripped corn oil") were examined. These samples were filled into an open beaker with a diameter of respectively 8.6 cm. To four of the samples there was then added with stirring for 10 minutes respectively one of the four ethanolic extracts of the wheat germ roasted at different temperatures (dosage 20%, see remarks in Example 2). No antioxidative ethanolic extract was added to the fifth sample and this served for control purposes.

The five samples were stored in a dry chamber at 50° C. The oxidative stability of the various samples was determined by repeated analysis, wherein respectively at intervals of multiple days (beginning after one day) the concentration of conjugated diene-hydroperoxides was determined, see FIG. 31.

Figure 31:
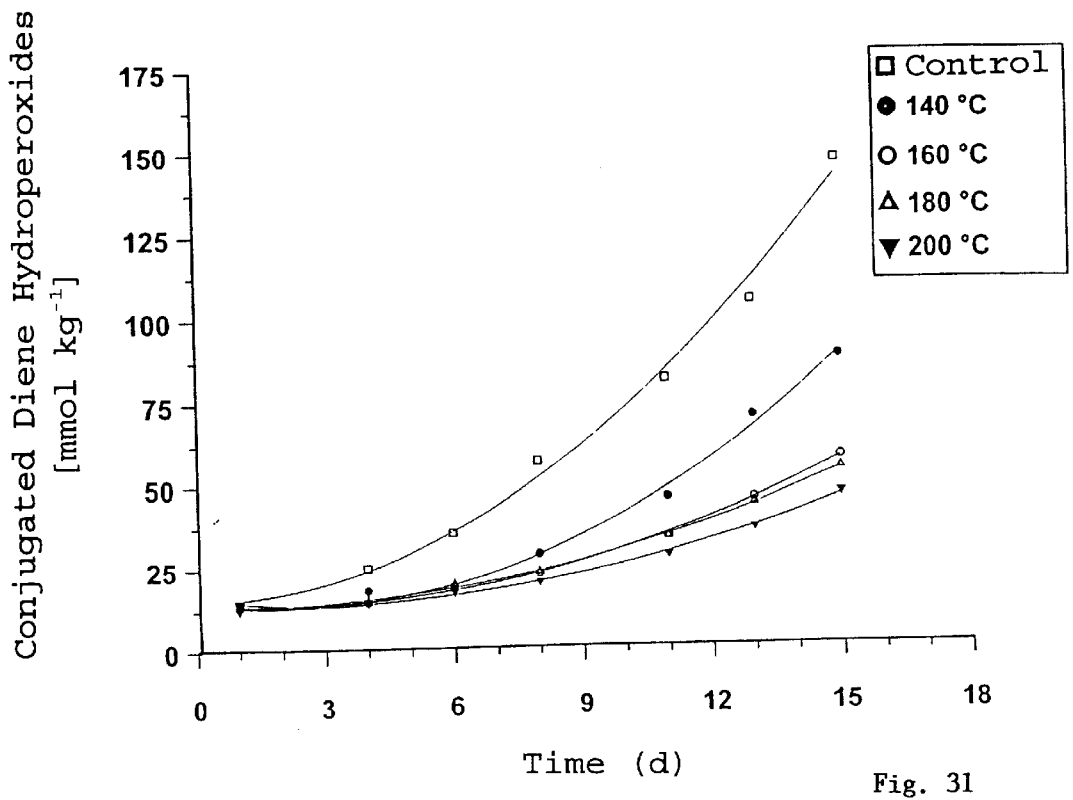
FIG. 31 Concentration of conjugated diene-hydroperoxides in tocopherol-free corn oil, which was stored at 50° C. with various ethanolic extracts of wheat germ, which were roasted at varying temperatures.

There is shown:

FIG. 31 Concentration of conjugated diene-hydroperoxides in tocopherol-free corn oil, which was stored at 50° C. with various ethanolic extracts of wheat germ, which were roasted at varying temperatures.

(Control=Control sample: the indicated temperatures associated with the measurement points in FIG. 31 indicate the roasting temperature of the associated samples)

FIG. 31 shows that the antioxidative effect of the ethanolic extract increases with increasing roasting temperature of the underlying wheat germ. At roasting temperatures above approximately 160° C. the improvements, in comparison with the extract of wheat germ which was roasted at lower temperatures, begin however to be less pronounced. An increase in the roasting temperature above the temperature of 160° C. thus brings about only small improvements with respect to the antioxidative characteristics of the corresponding extract. At roasting temperatures from above 160–170° C. there occurs instead a stronger formation of suspected toxicological pyrolysis products (IQ-compounds, that is, mutagenic hetercyclic aromatic amines); for this reason higher roasting temperatures are not particularly desired.

EXAMPLE 11

Testing for Researching the Influence of the Extraction Process on the Antioxidative Effect of a Corresponding Ethanolic Extract Two ethanolic extracts prepared in different manner from roasted wheat germ according to Example 1 b) were compared, namely:

(a) an extract according to Example 2 c) and
(b) an ethanolic Soxhlet-extract, which after 20 hours of continuous Soxhlet-extraction of 40 g roasted wheat germ according to Example 1 b) with ethanol at approximately 2 passes per hour was obtained by a subsequent concentration according to Example 2.

Analogous to Example 4, there were then tested 3 samples of respectively 50 g tocopherol-free corn oil ("stripped corn oil"). These samples were filled into an open beaker with a diameter of respectively 8.6 cm. Ethanolic extracts produced in respectively one of the two different ways was added with stirring for 10 minutes to the two samples (dosage 20%, see remarks in Example 2). Ethanolic extract was not added to the third sample and this served for control purposes.

The samples were stored at 50° C. in a dry chamber. The oxidative stability of the various samples was determined by repeated analysis wherein in intervals of multiple days respectively the concentration of conjugated diene-hydroperoxides was determined, see FIG. 32.

Figure 32:
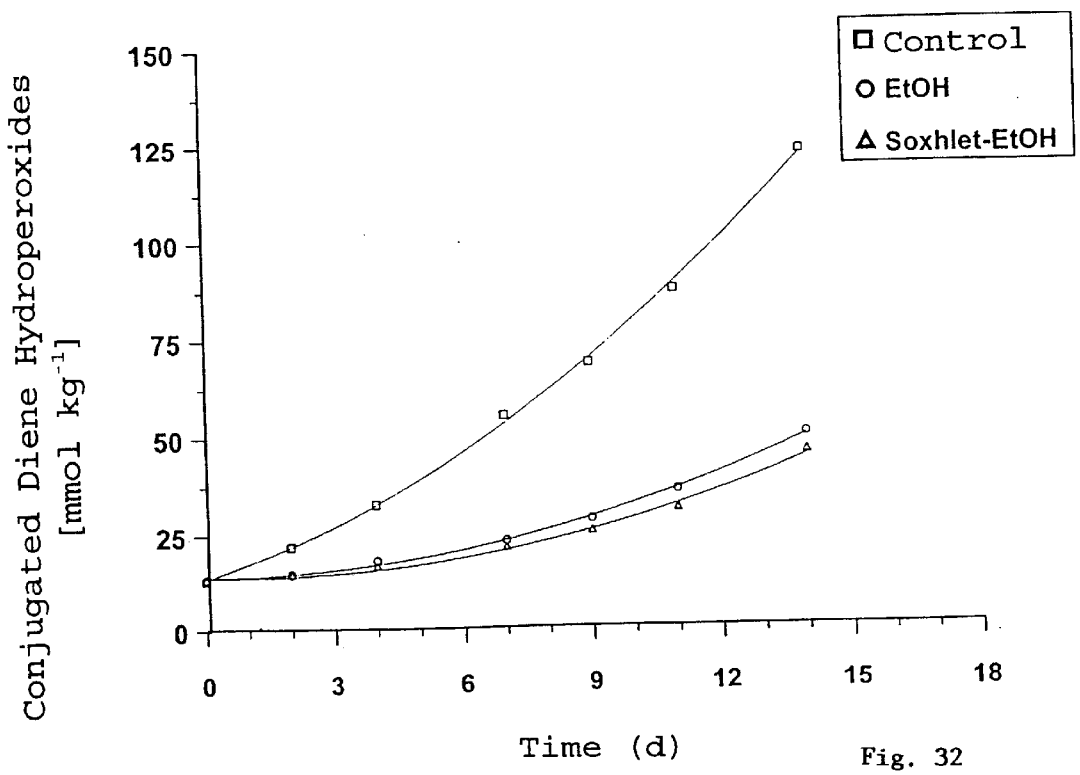
FIG. 32 Concentration of conjugated diene-hydroperoxides in tocopherol-free corn oil, which was stored at 50° C. with ethanolic extracts obtained in varying manners.

There is shown:

FIG. 32 Concentration of conjugated diene-hydroperoxides in tocopherol-free corn oil, which was stored at 50° C. with ethanolic extracts obtained in varying manners.

(Control=control samples; EtOH=ethanolic extract according to Example 2c; Soxhlet-EtOH=ethanolic Soxhlet-extract according to Example 11b)

From FIG. 32 it can be seen that a continuous extraction of roasted wheat germ (plot Soxhlet-EtOH) in comparison with an extraction according to Example 2 c) (plot EtOH) does not result in a clear increase in the antioxidative effect of the resulting extract.

EXAMPLE 12

Test for Determining the Influence of the Extract Amount on the Oxidative Effect of an Ethanolic Soxhlet-Extract An ethanolic Soxhlet-extract was employed, which was produced according to Example 11 b).

Analogously to Example 4, five samples of respectively 50 g tocopherol-free corn oil ("stripped corn oil") were tested. These samples were filled into an open beaker with a diameter of respectively 8.6 cm. To four of the samples there was then added, with stirring for 10 minutes, different amounts of a Soxhlet-extract, and namely (a) 5% Soxhlet-extract (b) 10% Soxhlet-extract (c) 20 Soxhlet-extract (d) 40% Soxhlet-extract, respectively according to the remarks in Example 2.

Ethanolic Soxhlet-extract was not added to the fifth sample and this served for control purposes.

The samples were stored at 50° C. in a dry chamber. The oxidative stability of the various samples was determined by repeated analysis, wherein at intervals of several days respectively the concentration of conjugated diene-hydroperoxides was determined, see FIG. 33.

Figure 33:
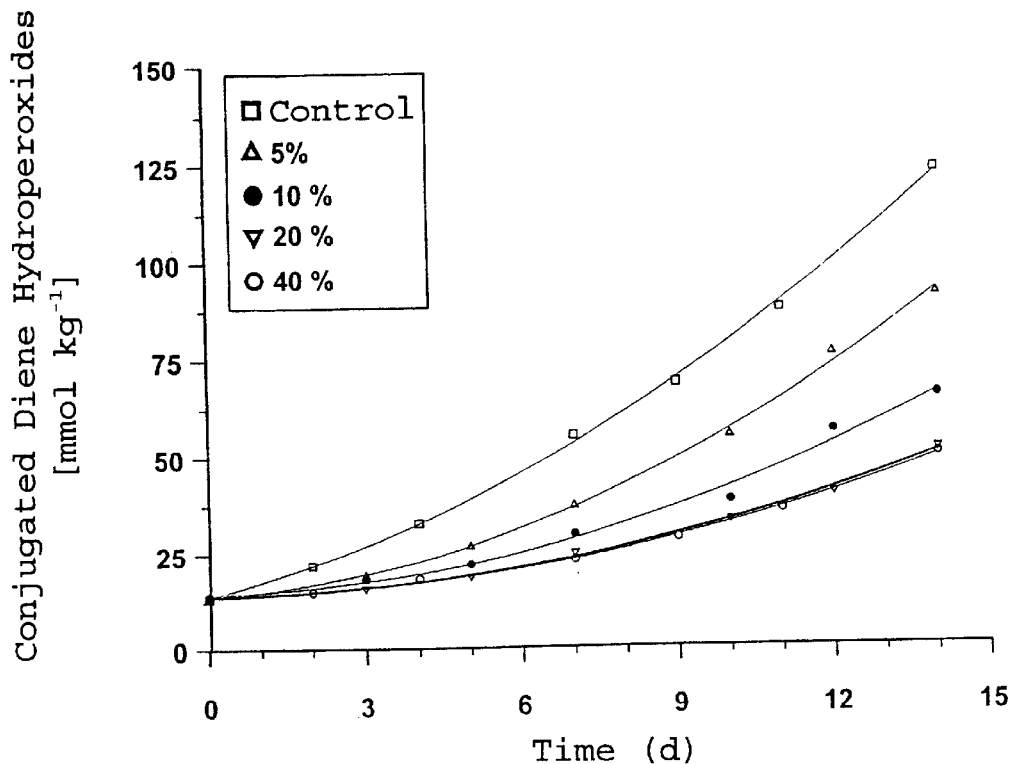
FIG. 33 Concentration of conjugated diene-hydroperoxides in tocopherol-free corn oil, which was stored at 50° C. with various amounts of an ethanolic Soxhlet-extract.

There is shown:

FIG. 33 Concentration of conjugated diene-hydroperoxides in tocopherol-free corn oil, which was stored at 50° C. with various amounts of an ethanolic Soxhlet-extract.

(Control=control sample; the percentages associates with the measuring points in Example 31 [sic] indicate the different employed amounts of extract)

From FIG. 33 it can be seen that the variation of the extract amounts of 5% to 10% brings about a significant improvement in the antioxidative effect.

In the transition from 10% to 20% the improvement in antioxidative effect is however only small.

In the transition from 20% to 40% no significant improvement in the antioxidative effect can any longer be determined.

EXAMPLE 13

Comparative Test for Stabilization of Tocopherol-free Corn Oil with Ethanolic Extracts of Different Roasted Grain Types There was tested a) an ethanolic extract according to Example 2 c), that is, an extract based upon the roasted wheat germ according to Example 1 b), as well as b) an ethanolic extract of roasted corn germ, which was produced from roasted corn germ analogous to Example 2 c), which were roasted analogously to Example 1 b), c) an ethanolic extract roasted barley germ, which was produced analogously to Example 2 c) from roasted barley germ, which was roasted analogously to Example 1 b), and as further comparative substance there was used d) ascorbylpalmitate.

Four samples of respectively 50 g tocopherol-free corn oil ("stripped corn oil") were examined. These samples were filled into open beakers with a diameter of respectively 8.6 cm. To the three examples there were added the antioxidants described under paragraphs a)–c) with stirring for 10 minutes, that is with wheat germ extract, corn germ extract and barley germ extract (dosing respectively 20%, see the remarks for Example 2) or as the case may be ascorbylpalmitate (dosing 0.02 weight %). No antioxidant was added to the fifth sample and this served for control purposes.

The samples were stored at 50° C. The oxidative stability of the various samples was determined by repeated analysis, wherein at intervals of several days (beginning after the first day) respectively the concentration of conjugated diene-hydroperoxides was determined, see FIG. 34.

Figure 34:
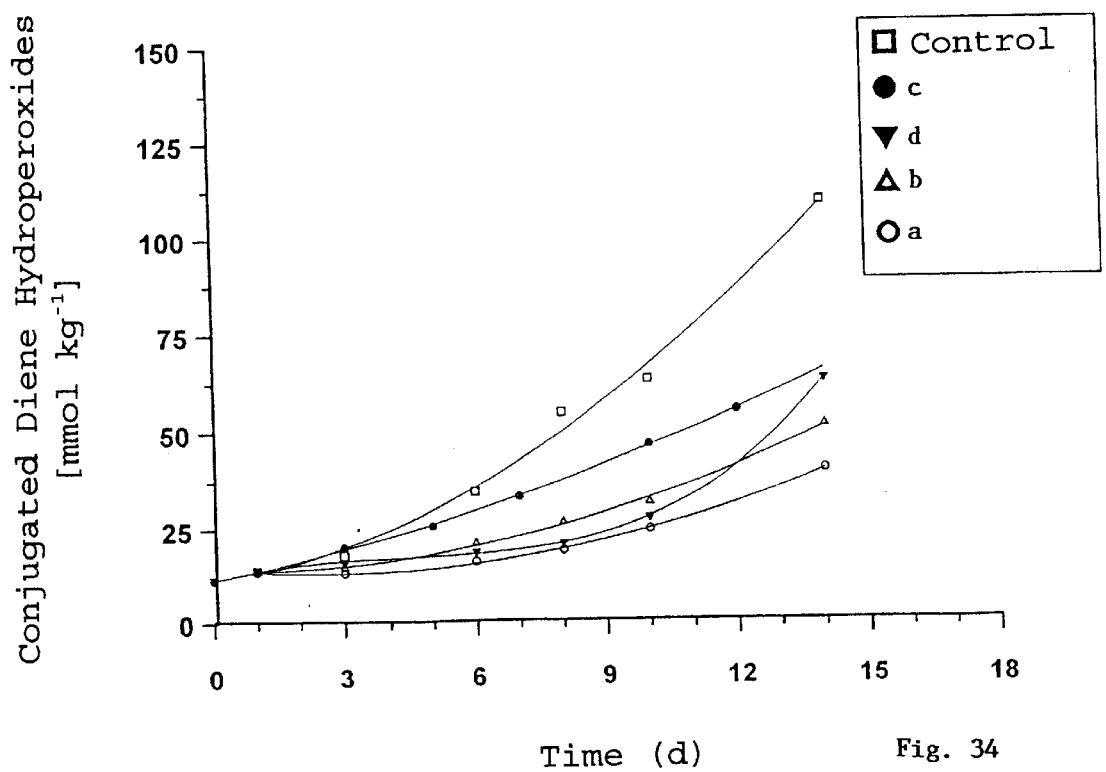
FIG. 34 Concentration of conjugated diene-hydroperoxides in tocopherol-free corn oil, which was stored at 50° C. with various antioxidants.

There is shown:

FIG. 34 Concentration of conjugated diene-hydroperoxides in tocopherol-free corn oil, which was stored at 50° C. with various antioxidants.

(Control=control sample; a=wheat germ extract; b=corn germ extract; c=barley germ extract; d=ascorbylpalmitate)

From FIG. 34 can be seen that not only the wheat germ extract, but rather also the corn germ extract and the barley germ extract have a significant antioxidative effect.

Ascorbylpalmitate demonstrated an antioxidative effect at the storage temperature of 50° C., which for the first 10 days was somewhat weaker than the wheat germ extract, however strong than the barley or corn germ extract. The rapid advance in the autooxidation from the $10^{th}$ to the $14^{th}$ day and the extrapolation of the curve for ascorbylpalmitate beyond the $14^{th}$ day however allows one to expect a pro-oxidative action at a later point in time. This is in agreement with the observed pro-oxidative effect of the ascorbylpalmitate in Example 4.

The tested extracts of wheat, barley and corn germ do not lead to expectation of pro-oxidative effect, even after longer storage times.

What is claimed is:

1. Foodstuff or cosmetic agent, including a stabilizing effective amount of an extract obtained by a process comprising:

extracting non-enzymatically browned grain germ separated from other components of whole grain with a solvent or solvent mixture having a $E_T^N$-value of between 0.6 and 0.8, followed by optionally separating the extraction agent.

2. An antioxidatively effective extract for stabilization of foodstuffs, wherein the extract is produced by a process comprising:

extracting non-enzymatically browned grain germ separated from other components of whole grain with a solvent or solvent mixture having a $E_T^N$-value of between 0.6 and 0.8 as extraction agent, collecting said extract and extraction agent, followed by optionally separating the extraction agent.

3. Process for production of an antioxidatively effective extract, comprising:

extracting non-enzymatically browned grain germ, separated prior to non-enzymatic browning from other components of whole grain, with a solvent or solvent mixture having a $E_T^N$-value of between 0.6 and 0.8 as extraction agent, collecting said extract and extraction agent, followed by optionally separating the extraction agent.

4. Process according to claim 3, wherein the extraction agent is selected from the group consisting of ethanol and ethanolic solutions.

5. Process according to claim 3, wherein the grain germ is selected from the group consisting of wheat, barley and corn germ.

6. Process according to claim 3, wherein said extract is subjected to fractionation, whereby aroma and/or color imparting minor ingredients of the extract are separated therefrom.

7. Process for production of an antioxidatively effective extract, comprising:

extracting roasted grain germ, separated prior to roasting from other components of whole grain, with a solvent or solvent mixture having a $E_T^N$-value of between 0.6 and 0.8 as extraction agent, collecting said extract and extraction agent, followed by optionally separating the extraction agent.

8. Process according to claim 7, wherein the grain germ is browned at a roasting temperature in the range of between 120° C. and 170° C.

9. Process according to claim 8, wherein the grain germ is browned at a roasting temperature in the range of between 140° C. and 160° C.

10. Process for stabilization of foodstuffs or cosmetic agents, comprising:

extracting non-enzymatically browned grain germ separated from other components of whole grain with a solvent or solvent mixture having a $E_T^N$-value of between 0.6 and 0.88 as extraction agent, collecting said extract and extraction agent, followed by optionally separating the extraction agent, and treating the foodstuff or cosmetic agent with a stabilizing effective amount of the extract or fraction of the extract.

11. A process according to claim 10, wherein said foodstuff is a lipid rich foodstuff.

* * * * *